(12) United States Patent
Zhang et al.

(10) Patent No.: US 12,421,313 B2
(45) Date of Patent: Sep. 23, 2025

(54) COMBINED PHARMACEUTICAL COMPOSITION FOR TREATING TUMOR

(71) Applicants: CHIA TAI TIANQING PHARMACEUTICAL GROUP CO., LTD., Lianyungang (CN); NANJING SHUNXIN PHARMACEUTICALS CO., LTD. OF CHIATAI TIANQING PHARMACEUTICAL GROUP, Nanjing (CN)

(72) Inventors: Xiquan Zhang, Lianyungang (CN); Xunqiang Wang, Lianyungang (CN); Chaoqiang Yang, Lianyungang (CN); Yuchen Fan, Lianyungang (CN); Mengxue Fan, Lianyungang (CN); Fan Feng, Lianyungang (CN); Nan Su, Lianyungang (CN); Yao Liu, Lianyungang (CN); Chi Zhang, Lianyungang (CN); Hai Jiang, Lianyungang (CN)

(73) Assignees: Chia Tia Tianqing Pharmaceutical Group Co., Ltd., Lianyungang (CN); Nanjing Shunxin Pharmaceuticals Co., Ltd. of Chiatai Tianqing Pharmaceutical Group, Nanjing (CN)

(*) Notice: Subject to any disclaimer, the term of this patent is extended or adjusted under 35 U.S.C. 154(b) by 1016 days.

(21) Appl. No.: 17/425,006

(22) PCT Filed: Jan. 23, 2020

(86) PCT No.: PCT/CN2020/073957
§ 371 (c)(1),
(2) Date: Jul. 22, 2021

(87) PCT Pub. No.: WO2020/151759
PCT Pub. Date: Jul. 30, 2020

(65) Prior Publication Data
US 2022/0089742 A1   Mar. 24, 2022

(30) Foreign Application Priority Data

Jan. 25, 2019   (CN) .......................... 201910071392.3
Jan. 25, 2019   (CN) .......................... 201910071393.8
Jan. 25, 2019   (CN) .......................... 201910071605.2
Jan. 25, 2019   (CN) .......................... 201910071632.X

(51) Int. Cl.
*C07K 16/28* (2006.01)
*A61K 31/4709* (2006.01)
*A61P 35/00* (2006.01)

(52) U.S. Cl.
CPC ...... *C07K 16/2827* (2013.01); *A61K 31/4709* (2013.01); *A61P 35/00* (2018.01)

(58) Field of Classification Search
CPC ............ C07K 16/2827; C07K 2317/21; C07K 2317/76; C07K 2317/56; A61K 31/4709; A61K 39/395; A61K 45/06; A61K 39/3955; A61K 2039/545; A61K 2039/505; A61K 2300/00; A61P 35/00
See application file for complete search history.

(56) References Cited

U.S. PATENT DOCUMENTS

| | | |
|---|---|---|
| 10,435,470 B2 | 10/2019 | Zha |
| 2015/0118222 A1 | 4/2015 | Levy et al. |
| 2016/0108123 A1 | 4/2016 | Freeman et al. |
| 2016/0326138 A1 | 11/2016 | Chen et al. |
| 2017/0088626 A1 | 3/2017 | Jure-Kunkel |
| 2017/0204184 A1 | 7/2017 | Zha et al. |
| 2017/0340733 A1 | 11/2017 | Cao |
| 2018/0147279 A1 | 5/2018 | Dar |
| 2022/0175759 A1* | 6/2022 | Wang ............... A61K 31/4709 |
| 2023/0227556 A1* | 7/2023 | Yang ............... C07K 16/2827 424/133.1 |
| 2023/0263795 A1* | 8/2023 | Zhang ............... A61K 39/3955 424/174.1 |
| 2023/0285554 A1* | 9/2023 | Zhang ............... A61K 39/39558 |
| 2023/0310496 A1* | 10/2023 | Ichikawa ............... A61K 9/007 424/600 |
| 2024/0343807 A1* | 10/2024 | Zhang ............... A61K 31/4709 |

FOREIGN PATENT DOCUMENTS

| | | |
|---|---|---|
| CN | 106255510 A | 12/2016 |
| CN | 107001463 A | 8/2017 |
| CN | 107530434 A | 1/2018 |
| CN | 107750166 A | 3/2018 |
| CN | 108779180 A | 11/2018 |
| EP | 2125776 B1 | 7/2017 |
| JP | 2017523786 A | 8/2017 |

(Continued)

OTHER PUBLICATIONS

Han, et al., JAMA Oncol. 2018 4(11):1569 (Year: 2018).*
Sela-Culang, et al., Front. In Immunol. 2013; vol. 4 Article 302 (Year: 2013).*
Brahmer, et al, N Engl J Med 2012 366(26):2455 (Year: 2012).*
Yakubke H.D., Amino acids, peptides, proteins, M: World, (1985), 456 pp., (see pp. 93-94).
Tyagi R., Gupta M. N., "Use of Chemical Modification and Chemical Cross-linking to Stabilize Proteins (enzymes)", Biochemistry, (1998), vol. 63, No. 3, pp. 395-407, (17 pp.), Chemistry Department, Indian Institute of Technology, Hauz Khas, New Delhi Found Feb. 9, 2022: URL: https://biochemistrymoscow.com/ru/archive/1998/63-03-0395/].

(Continued)

*Primary Examiner* — Anne M. Gussow
*Assistant Examiner* — Sydney Van Druff
(74) *Attorney, Agent, or Firm* — NIXON PEABODY LLP

(57) ABSTRACT

The present application relates to the field of biomedicine, and relates to a combined pharmaceutical composition for treating biliary tract tumor, liver cancer, triple negative breast cancer or lung cancer. The combined pharmaceutical composition comprises an anti-PD-L1 antibody and anlotinib, and has good anti-biliary tract tumor, liver cancer, triple negative breast cancer or lung cancer activity.

20 Claims, No Drawings

Specification includes a Sequence Listing.

(56) References Cited

FOREIGN PATENT DOCUMENTS

| WO | WO-2016022630 A1 * | 2/2016 | ......... A61K 47/6803 |
|---|---|---|---|
| WO | WO 2016/141218 A1 | 9/2016 | |
| WO | WO2016205277 | 12/2016 | |
| WO | WO2017/161976 | 9/2017 | |

OTHER PUBLICATIONS

Corraliza-Gorjón I et al. "New strategies using antibody combinations to increase cancer treatment effectiveness", Frontiers in Immunology, (Dec. 21, 2017), vol. 8, Article 1804, Found May 4, 2022: URL: https://www.ncbi.nlm.nih.gov/pmc/articles/PMC5742572/].

Tallarida R. J., "Quantitative Methods for Assessing Drug Synergism", Genes & Cancer, vol. 2, No. 11, pp. 1003-1008, Found Mar. 14, 2022: URL: https://www.ncbi.nlm.nih.gov/pmc/articles//PMC3379564/].

Pertsev I.M. Pharmaceutical and biomedical aspects of drugs: in 2 volumes. vol. 1.—Kharkiv: UkrFA, 1999, 464 pages, (p. 253-255).

Han B. et al., "Effect of Anlotinib as a third-line or further treatment on overall survival of patients with advanced non-small cell Lung Cancer: The ALTER 0303 Phase 3 Randomized Clinical Trial", JAMA Oncology, (Nov. 2018), vol. 4, No. 11, pp. 1569-1575, Found Aug. 6, 2023: URL: https://jamanetwork.com/journals/jamaoncology/article-abstract/2696341].

Brahmer et al. "Safety and activity of anti-PD-L1 antibody in patients with advanced cancer." New England Journal of Medicine 366.26, Jun. 28, 2012, pp. 2455-2465.

Han et al. "Anlotinib as a third-line therapy in patients with refractory advanced non-small-cell lung cancer: a multicentre, randomised phase II trial (ALTER0302)." British journal of cancer 118.5, Feb. 13, 2018, pp. 654-661.

Chi, Y. et al., "Safety and Efficacy of Anlotinib, a Multikinase Aniogenesis Inhibitor, in Patients With Refractory Metastatic Soft Tissue Sarcoma," American Association for Cancer Research, Jun. 13, 2018 (17 pages).

He, C. et al., "Anlotinib induces hepatocellular carcinoma apoptosis and inhibits proliferation via Erk and Akt pathway," Biochemical and Biophysical Research Communications, 2018 (7 pages).

International Search Report in International Application No. PCT/CN2020/073957, mailed Apr. 21, 2020 (6 pages).

Rudikoff et al., "Single amino acid substitution altering antigen-binding specificity," PNAS, vol. 79, No. 6, pp. 1979-1983, Mar. 1982, (5 pages).

Tamura et al., "Structural Correlates of an Anticarcinoma Antibody: Identification of Specificity-Determining Residues (SDRs) and Development of a Minimally Immunogenic Antibody Variant vy Retention of SDRs Only," J. Immunol., vol. 164, No. 3, pp. 1432-1441, Feb. 2000, (11 pages).

* cited by examiner

COMBINED PHARMACEUTICAL COMPOSITION FOR TREATING TUMOR

REFERENCES TO RELATED APPLICATIONS

The present application is a U.S. national stage of PCT/CN2020/073957, filed on Jan. 23, 2020, which claims the benefit and priority to the Chinese Patent Application No. 201910071632. X filed with the China National Intellectual Property Administration on Jan. 25, 2019 the Chinese patent application No. 201910071605.2 filed with the China National Intellectual Property Administration on Jan. 25, 2019; the Chinese Patent Application No. 201910071393.8 filed with the China National Intellectual Property Administration on Jan. 25, 2019; and the Chinese patent application No. 201910071392.3 filed with the China National Intellectual Property Administration on Jan. 25, 2019, all of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jul. 20, 2021 is named "059541-080US-PX_SL.txt" and is 22,343 bytes in size.

TECHNICAL FIELD

The present application relates to the field of biological therapies, and particularly to a combined pharmaceutical composition for treating tumors.

BACKGROUND

Tyrosine kinase is a group of enzymes which catalyze the phosphorylation of tyrosine residues in proteins. It plays an important role in intracellular signal transduction, takes part in adjustment, signaling and development of normal cells, and is closely related to proliferation, differentiation, migration and apoptosis of tumor cells. Many receptor tyrosine kinases are related to tumorigenesis and can be classified as epidermal growth factor receptor (EGFR), platelet-derived growth factor receptor (PDGFR), vascular endothelial growth factor receptor (VEGFR), fibroblast growth factor receptor (FGFR) and the like according to the structure of extracellular domain PD-L1 (programmed death-ligand 1), also known as CD247 or B7-H1, is a ligand for programmed cell death protein 1 (PD-1). PD-L1 is highly expressed on the surface of various tumor cells, and the malignant degree and poor prognosis of tumors are closely related to the expression level of PD-L1. In a tumor microenvironment, PD-L1 on cancer cell surface inhibits the activation and proliferation of T cells, induces effector T cell exhaustion or anergy, promotes apoptosis of T cells, and stimulates the differentiation of helper T cells into regulatory T cells by binding to PD-1 or CD80 on T cell surface, thus preventing the killing effect of T cells on tumor cells. Anti-PD-L1 antibodies can prevent the related negative regulation signals from being initiated and transducted by blocking the interaction of PD-L1 with PD-1 and CD80, thereby avoiding inhibited activity of effector T cells in tumor microenvironment and enabling T cells to exert the functions of killing and inhibiting tumor cells. Anti-PD-L1 antibodies can directly act on tumor tissues, providing the antibody for high specificity and safety. WO2016022630 discloses anti-PD-L1 antibodies, which have higher affinity to PD-L1, and can significantly inhibit the interaction between PD-L1 and PD-1 on cell surface and promote T cells to secrete IL-2 and INF-γ. Although patients with proliferative diseases (for example, cancers) have many treatment options, there's still a need for more effective pharmaceutical agents for clinical use, in particular combined use of more than one drug.

BRIEF SUMMARY

In one aspect, the present application provides a combined pharmaceutical composition comprising an anti-PD-L1 antibody and anlotinib.

Furthermore, anlotinib is in the form of a free base, or in the form of a pharmaceutically acceptable salt thereof. For example, the pharmaceutically acceptable salt of anlotinib can be hydrochloride or dihydrochloride.

Furthermore, the anti-PD-L1 antibody comprises an amino acid sequence as follows: a heavy chain CDR1 region having at least 80% homology to an amino acid sequence set forth in SEQ ID NO: 1 or SEQ ID NO: 4; a heavy chain CDR2 region having at least 80% homology to an amino acid sequence set forth in SEQ ID NO: 2 or SEQ ID NO: 5; a heavy chain CDR3 region having at least 80% homology to an amino acid sequence set forth in SEQ ID NO: 3 or SEQ ID NO: 6; a light chain CDR1 region having at least 80% homology to an amino acid sequence set forth in SEQ ID NO: 7 or SEQ ID NO: 10; a light chain CDR2 region having at least 80% homology to an amino acid sequence set forth in SEQ ID NO: 8 or SEQ ID NO: 11; and a light chain CDR3 region having at least 80% homology to an amino acid sequence set forth in SEQ ID NO: 9 or SEQ ID NO: 12. Furthermore, the anti-PD-L1 antibody comprises an amino acid sequence as follows: a heavy chain CDR1 region selected from the group consisting of SEQ ID NO: 1 and SEQ ID NO: 4; a heavy chain CDR2 region selected from the group consisting of SEQ ID NO: 2 and SEQ ID NO: 5; a heavy chain CDR3 region selected from the group consisting of SEQ ID NO: 3 and SEQ ID NO: 6; a light chain CDR1 region selected from the group consisting of SEQ ID NO: 7 and SEQ ID NO: 10; a light chain CDR2 region selected from the group consisting of SEQ ID NO: 8 and SEQ ID NO: 11; and a light chain CDR3 region selected from the group consisting of SEQ ID NO: 9 and SEQ ID NO: 12. Furthermore, the anti-PD-L1 antibody comprises: a heavy chain CDR1 region having an amino acid sequence set forth in SEQ ID NO: 1; a heavy chain CDR2 region having an amino acid sequence set forth in SEQ ID NO: 2; a heavy chain CDR3 region having an amino acid sequence set forth in SEQ ID NO: 3; a light chain CDR1 region having an amino acid sequence set forth in SEQ ID NO: 7; a light chain CDR2 region having an amino acid sequence set forth in SEQ ID NO: 8; and a light chain CDR3 region having an amino acid sequence set forth in SEQ ID NO: 9. Furthermore, the anti-PD-L1 antibody comprises an amino acid sequence as follows: a heavy chain variable region having at least 80% homology to an amino acid sequence set forth in SEQ ID NO: 13 or SEQ ID NO: 14; and a light chain variable region having at least 80% homology to an amino acid sequence set forth in SEQ ID NO: 15 or SEQ ID NO: 16. Furthermore, the anti-PD-L1 antibody comprises: a heavy chain variable region selected from the group consisting of heavy chain variable regions of hu13C5-hIgG1, hu13C5-hIgG4, hu5G11-hIgG1 and hu5G11-hIgG4 humanized antibodies; and a light chain variable region selected from the group consisting of light chain variable regions of hu13C5-hIgG1, hu13C5-hIgG4, hu5G11-hIgG1 and hu5G11-hIgG4 humanized antibodies.

Furthermore, the combined pharmaceutical composition disclosed herein is packaged in a kit further comprising an instruction for combined use of the anti-PD-L1 antibody and anlotinib in treating a tumor in biliary system, liver cancer, triple negative breast cancer and/or lung cancer.

Furthermore, the present application provides a combined pharmaceutical composition, comprising a pharmaceutical composition containing 600-2400 mg of the anti-PD-L1 antibody and a pharmaceutical composition containing anlotinib in a single dose of 6 mg, 8 mg, 10 mg and/or 12 mg, wherein the pharmaceutical composition containing the anti-PD-L1 antibody is in a single dose or multiple doses.

Furthermore, the present application provides a combined pharmaceutical composition, comprising a pharmaceutical composition containing 600-2400 mg of the anti-PD-L1 antibody in multiple doses and a pharmaceutical composition containing anlotinib in a single dose of 6 mg, 8 mg, 10 mg and/or 12 mg.

Furthermore, the present application provides a combined pharmaceutical composition which is a formulation suitable for administration within a single treatment cycle (e.g., a 21-day treatment cycle), comprising a pharmaceutical composition containing 600-2400 mg of the anti-PD-L1 antibody and a pharmaceutical composition containing 84-168 mg of anlotinib.

Furthermore, the present application provides a combined pharmaceutical composition comprising the anti-PD-L1 antibody and the anlotinib in a weight ratio of (0.35-29):1, preferably (3.5-29):1, more preferably (3.5-14.5):1, and most preferably (7-14.5):1, wherein the anti-PD-L1 antibody and anlotinib are packaged either separately or together, and wherein anlotinib can be packaged in multiple aliquots (e.g., 2 aliquots, 7 aliquots, 14 aliquots, 28 aliquots, or more); the anti-PD-L1 antibody can be packaged in a single or multiple aliquots (e.g., 2 aliquots, 4 aliquots, or more).

In addition, the present application provides a combined pharmaceutical composition for use in treating a tumor in biliary system, liver cancer, triple negative breast cancer and/or lung cancer, comprising an anti-PD-L1 antibody and anlotinib. In addition, the present application further provides a method for treating a tumor in biliary system, liver cancer, triple negative breast cancer and/or lung cancer, comprising administering to a subject an effective amount of the combined pharmaceutical composition disclosed herein. In addition, the present application further provides use of the combined pharmaceutical composition in preparing a medicament for treating a tumor in biliary system, liver cancer, triple negative breast cancer and/or lung cancer. Alternatively, the present application further provides use of the anti-PD-L1 antibody and anlotinib in preparing a medicament for treating a tumor in biliary system, liver cancer, triple negative breast cancer and/or lung cancer.

Furthermore, the anti-PD-L1 antibody and anlotinib are each in a form of a pharmaceutical composition that can be administered simultaneously, sequentially or at intervals. Still further, the anti-PD-L1 antibody is administered once every week, every 2 weeks, every 3 weeks, or every 4 weeks; preferably, the anti-PD-L1 antibody is administered at a dose of 600-2400 mg. Still further, anlotinib is administered at a dose of 6 mg, 8 mg, 10 mg, or 12 mg once daily with a regimen of 2-week treatment plus 1-week interruption.

In addition, the present application provides a kit for treating a tumor in biliary system, liver cancer, triple negative breast cancer and/or lung cancer, comprising a pharmaceutical composition of an anti-PD-L1 antibody, a pharmaceutical composition of anlotinib, and an instruction for combined use of the anti-PD-L1 antibody and anlotinib in treating a tumor in biliary system, liver cancer, triple negative breast cancer and/or lung cancer.

Furthermore, the kit is suitable for administration within a single treatment cycle (e.g., a 21-day treatment cycle), comprising a pharmaceutical composition containing 600-2400 mg of the anti-PD-L1 antibody and a pharmaceutical composition containing 84-168 mg of anlotinib.

In a first aspect, the present application provides a combined pharmaceutical composition for use in treating a tumor in biliary system comprising an anti-PD-L1 antibody and anlotinib.

In another aspect, the present application further provides use of the combined pharmaceutical composition in preparing a medicament for treating a tumor in biliary system. The present application further provides a method for treating a tumor in biliary system, comprising administering to a subject an effective amount of the combined pharmaceutical composition disclosed herein. The present application also provides use of the combined pharmaceutical composition in treating a tumor in biliary system. The combined pharmaceutical composition comprises an anti-PD-L1 antibody and anlotinib.

In another aspect, the present application further provides use of a combination of the anti-PD-L1 antibody and anlotinib in preparing a medicament for treating a tumor in biliary system. The present application further provides a method for treating a tumor in biliary system, comprising administering to a subject effective amounts of the anti-PD-L1 antibody and anlotinib. The present application further provides use of a combination of the anti-PD-L1 antibody and anlotinib in treating a tumor in biliary system. The present application further provides a combination of the anti-PD-L1 antibody and anlotinib for use in treating a tumor in biliary system.

In a second aspect, the present application provides a combined pharmaceutical composition for use in treating liver cancer comprising an anti-PD-L1 antibody and anlotinib.

In another aspect, the present application further provides use of the combined pharmaceutical composition in preparing a medicament for treating liver cancer. The present application further provides a method for treating liver cancer, comprising administering to a subject an effective amount of the combined pharmaceutical composition disclosed herein. The present application also provides use of the combined pharmaceutical composition in treating liver cancer. The combined pharmaceutical composition comprises an anti-PD-L1 antibody and anlotinib.

In another aspect, the present application further provides use of a combination of the anti-PD-L1 antibody and anlotinib in preparing a medicament for treating liver cancer. The present application further provides a method for treating liver cancer, comprising administering to a subject an effective amount of the anti-PD-L1 antibody and anlotinib. The present application further provides use of a combination of the anti-PD-L1 antibody and anlotinib in treating liver cancer. The present application further provides a combination of the anti-PD-L1 antibody and anlotinib for use in treating liver cancer.

In a third aspect, the present application provides a combined pharmaceutical composition for use in treating triple negative breast cancer comprising an anti-PD-L1 antibody and anlotinib.

In another aspect, the present application further provides use of the combined pharmaceutical composition in preparing a medicament for treating triple negative breast cancer. The present application further provides a method for treating triple negative breast cancer, comprising administering to a subject an effective amount of the combined pharmaceutical composition disclosed herein. The present application also provides use of the combined pharmaceutical composition in treating triple negative breast cancer. The combined pharmaceutical composition comprises an anti-PD-L1 antibody and anlotinib.

In another aspect, the present application further provides use of a combination of the anti-PD-L1 antibody and anlotinib in preparing a medicament for treating triple negative breast cancer. The present application further provides a method for treating triple negative breast cancer, comprising administering to a subject effective amounts of the anti-PD-L1 antibody and anlotinib. The present application further provides use of a combination of the anti-PD-L1 antibody and anlotinib in treating triple negative breast cancer. The present application further provides a combination of the anti-PD-L1 antibody and anlotinib for use in treating triple negative breast cancer.

In a fourth aspect, the present application provides a combined pharmaceutical composition for use in treating lung cancer comprising an anti-PD-L1 antibody and anlotinib.

In another aspect, the present application further provides use of the combined pharmaceutical composition in preparing a medicament for treating lung cancer. The present application further provides a method for treating lung cancer, comprising administering to a subject an effective amount of the combined pharmaceutical composition disclosed herein. The present application also provides use of the combined pharmaceutical composition in treating lung cancer. The combined pharmaceutical composition comprises an anti-PD-L1 antibody and anlotinib.

In another aspect, the present application further provides use of a combination of the anti-PD-L1 antibody and anlotinib in preparing a medicament for treating lung cancer. The present application further provides a method for treating lung cancer, comprising administering to a subject effective amounts of the anti-PD-L1 antibody and anlotinib. The present application further provides use of a combination of the anti-PD-L1 antibody and anlotinib in treating lung cancer. The present application further provides a combination of the anti-PD-L1 antibody and anlotinib for use in treating lung cancer.

SUMMARY

The present application provides a combined pharmaceutical composition comprising an anti-PD-L1 antibody and anlotinib. In some embodiments of the present application, the combined pharmaceutical composition is used for treating a tumor or cancer. In some embodiments of the present application, the tumor or cancer is selected from the group consisting of a tumor in biliary system, liver cancer, triple negative breast cancer, and lung cancer.

Combined Pharmaceutical Composition for Treating Tumor in Biliary System

In one aspect, the present application provides a combined pharmaceutical composition for use in treating a tumor in biliary system comprising an anti-PD-L1 antibody and anlotinib.

In some embodiments of the present application, the combined pharmaceutical composition comprises a pharmaceutical composition of the anti-PD-L1 antibody and a pharmaceutical composition of anlotinib.

In some embodiments of the present application, the combined pharmaceutical composition is packaged in a kit further comprising an instruction for combined use of the anti-PD-L1 antibody and anlotinib in treating a tumor in biliary system.

In some embodiments, provided is a combined pharmaceutical composition for use in treating a tumor in biliary system, comprising a pharmaceutical composition containing 600-2400 mg of the anti-PD-L1 antibody and a pharmaceutical composition containing anlotinib in a single dose of 6 mg, 8 mg, 10 mg and/or 12 mg, wherein the pharmaceutical composition containing the anti-PD-L1 antibody is in a single dose or multiple doses.

In some embodiments, provided is a combined pharmaceutical composition for treating a tumor in biliary system, comprising a pharmaceutical composition containing 600-2400 mg of the anti-PD-L1 antibody in multiple doses and a pharmaceutical composition containing anlotinib in a single dose of 6 mg, 8 mg, 10 mg and/or 12 mg.

In some embodiments, provided is a combined pharmaceutical composition for use in treating a tumor in biliary system, comprising the anti-PD-L1 antibody and the anlotinib in a weight ratio of (0.35-29):1, preferably (3.5-29):1, more preferably (3.5-14.5):1, and most preferably (7-14.5):1, wherein the anti-PD-L1 antibody and anlotinib are packaged either separately or together, and wherein anlotinib can be packaged in multiple aliquots (e.g., 2 aliquots, 7 aliquots, 14 aliquots, 28 aliquots, or more).

In some embodiments, provided is a combined pharmaceutical composition for use in treating a tumor in biliary system, comprising a pharmaceutical composition of the anti-PD-L1 antibody and a pharmaceutical composition of anlotinib, wherein the pharmaceutical composition of the anti-PD-L1 antibody is formulated to be suitable for administration to a patient 600-2400 mg of the anti-PD-L1 antibody in a single dose or multiple doses at a first dose, and the pharmaceutical composition of anlotinib is formulated to be suitable for administration to a patient in a single dose of 6 mg, 8 mg, 10 mg, and/or 12 mg of anlotinib daily for 14 days.

In some embodiments, provided is a combined pharmaceutical composition for use in treating a tumor in biliary system, comprising a pharmaceutical composition of the anti-PD-L1 antibody containing 10-60 mg/mL of the anti-PD-L1 antibody and a pharmaceutical composition containing anlotinib in a single dose of 6 mg, 8 mg, 10 mg and/or 12 mg.

In some embodiments, provided is a combined pharmaceutical composition for use in treating a tumor in biliary system, comprising a pharmaceutical composition of the anti-PD-L1 antibody containing 10 mg/mL of the anti-PD-L1 antibody and a pharmaceutical composition containing anlotinib in a single dose of 8 mg and/or 10 mg.

In some embodiments, provided is a combined pharmaceutical composition for use in treating a tumor in biliary system, comprising a pharmaceutical composition containing 1200 mg of the anti-PD-L1 antibody in multiple doses and a pharmaceutical composition containing anlotinib in a single dose of 8 mg and/or 10 mg.

In another aspect, the present application further provides use of the combined pharmaceutical composition in preparing a medicament for treating a tumor in biliary system. The present application further provides a method for treating a tumor in biliary system, comprising administering to a subject an effective amount of the combined pharmaceutical composition disclosed herein. The present application also provides use of the combined pharmaceutical composition in treating a tumor in biliary system. In some embodiments, the combined pharmaceutical composition comprises a humanized anti-PD-L1 monoclonal antibody and anlotinib.

In another aspect, the present application further provides use of a composition of the anti-PD-L1 antibody and anlotinib in preparing a medicament for treating a tumor in biliary system. The present application further provides a method for treating a tumor in biliary system, comprising administering to a subject an effective amount of the composition of the anti-PD-L1 antibody and anlotinib. The present application further provides use of the composition of the anti-PD-L1 antibody and anlotinib in treating a tumor in biliary system.

In yet another aspect, the present application provides a kit for use in treating a tumor in biliary system, comprising a pharmaceutical composition of an anti-PD-L1 antibody, a pharmaceutical composition of anlotinib, and an instruction for combined use of the anti-PD-L1 antibody and anlotinib in treating a tumor in biliary system.

In yet another aspect, the present application further provides an anti-PD-L1 antibody for use in treating a tumor in biliary system. The present application further provides a method for treating a tumor in biliary system, comprising administering to a subject an effective amount of the anti-PD-L1 antibody disclosed herein. The present application further provides use of the anti-PD-L1 antibody in treating a tumor in biliary system. The present application further provides use of the anti-PD-L1 antibody in preparing a medicament for treating a tumor in biliary system.

Combined Pharmaceutical Composition for Treating Liver Cancer

In one aspect, the present application provides a combined pharmaceutical composition for use in treating liver cancer comprising an anti-PD-L1 antibody and anlotinib.

In some embodiments of the present application, the combined pharmaceutical composition comprises a pharmaceutical composition of the anti-PD-L1 antibody and a pharmaceutical composition of anlotinib.

In some embodiments of the present application, the combined pharmaceutical composition is packaged in a kit further comprising an instruction for combined use of the anti-PD-L1 antibody and anlotinib in treating liver cancer.

In some embodiments, provided is a combined pharmaceutical composition for use in treating liver cancer, comprising a pharmaceutical composition containing 600-2400 mg of the anti-PD-L1 antibody and a pharmaceutical composition containing anlotinib in a single dose of 6 mg, 8 mg, 10 mg and/or 12 mg, wherein the pharmaceutical composition containing the anti-PD-L1 antibody is in a single dose or multiple doses.

In some embodiments, provided is a combined pharmaceutical composition for use in treating liver cancer, comprising a pharmaceutical composition containing 600-2400 mg of the anti-PD-L1 antibody in multiple doses and a pharmaceutical composition containing anlotinib in a single dose of 6 mg, 8 mg, 10 mg and/or 12 mg.

In some embodiments, provided is a combined pharmaceutical composition for use in treating liver cancer, comprising the anti-PD-L1 antibody and the anlotinib in a weight ratio of (0.35-29):1, preferably (3.5-29):1, more preferably (3.5-14.5):1, and most preferably (7-14.5):1, wherein the anti-PD-L1 antibody and anlotinib are packaged either separately or together, and wherein anlotinib can be packaged in multiple aliquots (e.g., 2 aliquots, 7 aliquots, 14 aliquots, 28 aliquots, or more).

In some embodiments, provided is a combined pharmaceutical composition for use in treating liver cancer, comprising a pharmaceutical composition of the anti-PD-L1 antibody and a pharmaceutical composition of anlotinib, wherein the pharmaceutical composition of the anti-PD-L1 antibody is formulated to be suitable for administration to a patient 600-2400 mg of the anti-PD-L1 antibody in a single dose or multiple doses at a first dose, and the pharmaceutical composition of anlotinib is formulated to be suitable for administration to a patient in a single dose of 6 mg, 8 mg, 10 mg, and/or 12 mg of anlotinib daily for 14 days.

In some embodiments, provided is a combined pharmaceutical composition for use in treating liver cancer, comprising a pharmaceutical composition of the anti-PD-L1 antibody containing 10-60 mg/mL of the anti-PD-L1 antibody and a pharmaceutical composition containing anlotinib in a single dose of 6 mg, 8 mg, 10 mg and/or 12 mg.

In some embodiments, provided is a combined pharmaceutical composition for use in treating liver cancer, comprising a pharmaceutical composition of the anti-PD-L1 antibody containing 10 mg/mL of the anti-PD-L1 antibody and a pharmaceutical composition containing anlotinib in a single dose of 8 mg and/or 10 mg.

In some embodiments, provided is a combined pharmaceutical composition for use in treating liver cancer, comprising a pharmaceutical composition containing 1200 mg of the anti-PD-L1 antibody in multiple doses and a pharmaceutical composition containing anlotinib in a single dose of 8 mg and/or 10 mg.

In another aspect, the present application further provides use of the combined pharmaceutical composition in preparing a medicament for treating liver cancer. The present application further provides a method for treating liver cancer, comprising administering to a subject an effective amount of the combined pharmaceutical composition disclosed herein. The present application also provides use of the combined pharmaceutical composition in treating liver cancer. In some embodiments, the combined pharmaceutical composition comprises a humanized anti-PD-L1 monoclonal antibody and anlotinib.

In another aspect, the present application further provides use of a composition of the anti-PD-L1 antibody and anlotinib in preparing a medicament for treating liver cancer. The present application further provides a method for treating liver cancer, comprising administering to a subject an effective amount of the composition of the anti-PD-L1 antibody and anlotinib. The present application further provides use of the composition of the anti-PD-L1 antibody and anlotinib in treating liver cancer.

In yet another aspect, the present application provides a kit for treating liver cancer, comprising a pharmaceutical composition of an anti-PD-L1 antibody, a pharmaceutical composition of anlotinib, and an instruction for combined use of the anti-PD-L1 antibody and anlotinib in treating liver cancer.

In yet another aspect, the present application further provides an anti-PD-L1 antibody for use in treating liver cancer. The present application further provides a method for treating liver cancer, comprising administering to a subject an effective amount of the anti-PD-L1 antibody disclosed herein. The present application further provides use of the anti-PD-L1 antibody in treating liver cancer. The present application further provides use of the anti-PD-L1 antibody in preparing a medicament for treating liver cancer.

Combined Pharmaceutical Composition for Treating Triple Negative Breast Cancer

In one aspect, the present application provides a combined pharmaceutical composition for use in treating triple negative breast cancer comprising an anti-PD-L1 antibody and anlotinib.

In some embodiments of the present application, the combined pharmaceutical composition comprises a pharmaceutical composition of the anti-PD-L1 antibody and a pharmaceutical composition of anlotinib.

In some embodiments of the present application, the combined pharmaceutical composition is packaged in a kit further comprising an instruction for combined use of the anti-PD-L1 antibody and anlotinib in treating triple negative breast cancer.

In some embodiments, provided is a combined pharmaceutical composition for use in treating triple negative breast cancer, comprising a pharmaceutical composition containing 600-2400 mg of the anti-PD-L1 antibody and a pharmaceutical composition containing anlotinib in a single dose of 6 mg, 8 mg, 10 mg and/or 12 mg, wherein the pharmaceutical composition containing the anti-PD-L1 antibody is in a single dose or multiple doses.

In some embodiments, provided is a combined pharmaceutical composition for use in treating triple negative breast cancer, comprising a pharmaceutical composition containing 600-2400 mg of the anti-PD-L1 antibody in multiple doses and a pharmaceutical composition containing anlotinib in a single dose of 6 mg, 8 mg, 10 mg and/or 12 mg.

In some embodiments, provided is a combined pharmaceutical composition for use in treating triple negative breast cancer, comprising the anti-PD-L1 antibody and the anlotinib in a weight ratio of (0.35-29):1, preferably (3.5-29):1, more preferably (3.5-14.5):1, and most preferably (7-14.5):1, wherein the anti-PD-L1 antibody and anlotinib are packaged either separately or together, and wherein anlotinib can be packaged in multiple aliquots (e.g., 2 aliquots, 7 aliquots, 14 aliquots, 28 aliquots, or more).

In some embodiments, provided is a combined pharmaceutical composition for use in treating triple negative breast cancer, comprising a pharmaceutical composition of the anti-PD-L1 antibody and a pharmaceutical composition of anlotinib, wherein the pharmaceutical composition of the anti-PD-L1 antibody is formulated to be suitable for administration to a patient 600-2400 mg of the anti-PD-L1 antibody in a single dose or multiple doses at a first dose, and the pharmaceutical composition of anlotinib is formulated to be suitable for administration to a patient in a single dose of 6 mg, 8 mg, 10 mg, and/or 12 mg of anlotinib daily for 14 days.

In some embodiments, provided is a combined pharmaceutical composition for use in treating triple negative breast cancer, comprising a pharmaceutical composition of the anti-PD-L1 antibody containing 10-60 mg/mL of the anti-PD-L1 antibody and a pharmaceutical composition containing anlotinib in a single dose of 6 mg, 8 mg, 10 mg and/or 12 mg.

In some embodiments, provided is a combined pharmaceutical composition for use in treating triple negative breast cancer, comprising a pharmaceutical composition of the anti-PD-L1 antibody containing 10 mg/mL of the anti-PD-L1 antibody and a pharmaceutical composition containing anlotinib in a single dose of 8 mg and/or 10 mg.

In some embodiments, provided is a combined pharmaceutical composition for use in treating triple negative breast cancer, comprising a pharmaceutical composition containing 1200 mg of the anti-PD-L1 antibody in multiple doses and a pharmaceutical composition containing anlotinib in a single dose of 8 mg and/or 10 mg.

In another aspect, the present application further provides use of the combined pharmaceutical composition in preparing a medicament for treating triple negative breast cancer. The present application further provides a method for treating triple negative breast cancer, comprising administering to a subject an effective amount of the combined pharmaceutical composition disclosed herein. The present application also provides use of the combined pharmaceutical composition in treating triple negative breast cancer. In some embodiments, the combined pharmaceutical composition comprises a humanized anti-PD-L1 monoclonal antibody and anlotinib.

In another aspect, the present application further provides use of a composition of the anti-PD-L1 antibody and anlotinib in preparing a medicament for treating triple negative breast cancer. The present application further provides a method for treating triple negative breast cancer, comprising administering to a subject an effective amount of the composition of the anti-PD-L1 antibody and anlotinib. The present application further provides use of the composition of the anti-PD-L1 antibody and anlotinib in treating triple negative breast cancer.

In yet another aspect, the present application provides a kit for treating triple negative breast cancer, comprising a pharmaceutical composition of an anti-PD-L1 antibody, a pharmaceutical composition of anlotinib, and an instruction for combined use of the anti-PD-L1 antibody and anlotinib in treating triple negative breast cancer.

In yet another aspect, the present application further provides an anti-PD-L1 antibody for use in treating triple negative breast cancer. The present application further provides a method for treating triple negative breast cancer, comprising administering to a subject an effective amount of the anti-PD-L1 antibody disclosed herein. The present application further provides use of the anti-PD-L1 antibody in treating triple negative breast cancer. The present application further provides use of the anti-PD-L1 antibody in preparing a medicament for treating triple negative breast cancer.

Combined Pharmaceutical Composition for Treating Lung Cancer

In one aspect, the present application provides a combined pharmaceutical composition for use in treating lung cancer comprising an anti-PD-L1 antibody and anlotinib.

In some embodiments of the present application, the combined pharmaceutical composition comprises a pharmaceutical composition of the anti-PD-L1 antibody and a pharmaceutical composition of anlotinib.

In some embodiments of the present application, the combined pharmaceutical composition is packaged in a kit further comprising an instruction for combined use of the anti-PD-L1 antibody and anlotinib in treating lung cancer.

In some embodiments, provided is a combined pharmaceutical composition for use in treating lung cancer, comprising a pharmaceutical composition containing 600-2400 mg of the anti-PD-L1 antibody and a pharmaceutical composition containing anlotinib in a single dose of 6 mg, 8 mg, 10 mg and/or 12 mg, wherein the pharmaceutical composition containing the anti-PD-L1 antibody is in a single dose or multiple doses.

In some embodiments, provided is a combined pharmaceutical composition for use in treating lung cancer, comprising a pharmaceutical composition containing 600-2400 mg of the anti-PD-L1 antibody in multiple doses and a pharmaceutical composition containing anlotinib in a single dose of 6 mg, 8 mg, 10 mg and/or 12 mg.

In some embodiments, provided is a combined pharmaceutical composition for use in treating lung cancer, comprising a pharmaceutical composition of the anti-PD-L1 antibody and a pharmaceutical composition of anlotinib, wherein the pharmaceutical composition of the anti-PD-L1 antibody is formulated to be suitable for administration to a patient 600-2400 mg of the anti-PD-L1 antibody in a single dose or multiple doses at a first dose, and the pharmaceutical composition of anlotinib is formulated to be suitable for administration to a patient in a single dose of 6 mg, 8 mg, 10 mg, and/or 12 mg of anlotinib daily for 14 days.

In some embodiments, provided is a combined pharmaceutical composition for use in treating lung cancer, comprising a pharmaceutical composition of the anti-PD-L1 antibody containing 10-60 mg/mL of the anti-PD-L1 antibody and a pharmaceutical composition containing anlotinib in a single dose of 6 mg, 8 mg, 10 mg and/or 12 mg.

In some embodiments, provided is a combined pharmaceutical composition for use in treating lung cancer, comprising the anti-PD-L1 antibody and the anlotinib in a weight ratio of (0.35-29):1, preferably (3.5-29):1, more preferably (3.5-14.5):1, and most preferably (7-14.5):1, wherein the anti-PD-L1 antibody and anlotinib are packaged either separately or together, and wherein anlotinib can be packaged in multiple aliquots (e.g., 2 aliquots, 7 aliquots, 14 aliquots, 28 aliquots, or more).

In some embodiments, provided is a combined pharmaceutical composition for use in treating lung cancer, comprising a pharmaceutical composition of the anti-PD-L1 antibody containing 10 mg/mL of the anti-PD-L1 antibody and a pharmaceutical composition containing anlotinib in a single dose of 8 mg and/or 10 mg.

In some embodiments, provided is a combined pharmaceutical composition for use in treating lung cancer, comprising a pharmaceutical composition containing 1200 mg of the anti-PD-L1 antibody in multiple doses and a pharmaceutical composition containing anlotinib in a single dose of 8 mg and/or 10 mg.

In another aspect, the present application further provides use of the combined pharmaceutical composition in preparing a medicament for use in treating lung cancer. The present application further provides a method for treating lung cancer, comprising administering to a subject an effective amount of the combined pharmaceutical composition disclosed herein. The present application also provides use of the combined pharmaceutical composition in treating lung cancer. The combined pharmaceutical composition comprises a humanized anti-PD-L1 monoclonal antibody and anlotinib.

In another aspect, the present application further provides use of a composition of the anti-PD-L1 antibody and anlotinib in preparing a medicament for treating lung cancer. The present application further provides a method for treating lung cancer, comprising administering to a subject an effective amount of the composition of the anti-PD-L1 antibody and anlotinib. The present application further provides use of the composition of the anti-PD-L1 antibody and anlotinib in treating lung cancer.

In yet another aspect, the present application provides a kit for treating lung cancer, comprising a pharmaceutical composition of an anti-PD-L1 antibody, a pharmaceutical composition of anlotinib, and an instruction for combined use of the anti-PD-L1 antibody and anlotinib in treating lung cancer.

In yet another aspect, the present application further provides an anti-PD-L1 antibody for use in treating lung cancer. The present application further provides a method for treating lung cancer, comprising administering to a subject an effective amount of the anti-PD-L1 antibody disclosed herein. The present application further provides use of the anti-PD-L1 antibody in treating lung cancer. The present application further provides use of the anti-PD-L1 antibody in preparing a medicament for treating lung cancer.

Dosage Regimen/Treatment Regimen of Combined Pharmaceutical Composition

In some embodiments of the present application, for the above use or methods for treatment, the anti-PD-L1 antibody and anlotinib are each in the form of a pharmaceutical composition that can be administered simultaneously, sequentially or at intervals.

In some embodiments of the present application, for the above use or methods for treatment, the anti-PD-L1 antibody and anlotinib are separately administered at intervals. In some embodiments, the antibody and the anlotinib are administered separately on the same or different regimens. In some embodiments, the two are separately administered on different regimens.

In some embodiments of the present application, for the above use or methods for treatment, the anti-PD-L1 antibody can be administered once every week (q1w), every 2 weeks (q2w), every 3 weeks (q3w), or every 4 weeks (q4w). In one specific embodiment, the anti-PD-L1 antibody is administered once every 3 weeks. In some embodiments, the anti-PD-L1 antibody is administered at a dose of 600-2400 mg each time.

Anlotinib can be administered at a dose of 6 mg, 8 mg, 10 mg, or 12 mg once daily with a regimen of continuous 2-week treatment plus 1-week interruption.

In some embodiments, the anti-PD-L1 antibody and anlotinib have the same or different treatment cycles. In some specific embodiments, the anti-PD-L1 antibody and anlotinib have the same treatment cycle, e.g., a 1-week, 2-week, 3-week or 4-week treatment cycle.

In some embodiments of the present application, for the use or methods for treatment, a treatment cycle takes 21 days; the anti-PD-L1 antibody is administered on the first day of each cycle and anlotinib is administered daily on days 1-14 of each cycle. In one specific embodiment, the anti-PD-L1 antibody is administered once on the first day of each cycle and anlotinib is administered once daily on days 1-14 of each cycle.

In some embodiments of the present application, for the use or methods for treatment, the anti-PD-L1 antibody may be administered to the subject at a dose selected from the group consisting of: 0.01 to 40 mg/kg, 0.1 to 30 mg/kg, 0.1 to 20 mg/kg, 0.1 to 15 mg/kg, 0.1 to 10 mg/kg, 1 to 15 mg/kg, 1 to 20 mg/kg, 1 to 3 mg/kg, 3 to 10 mg/kg, 3 to 15 mg/kg, 3 to 20 mg/kg, 3 to 30 mg/kg, 10 to 20 mg/kg and 15 to 20 mg/kg; or administered to the subject at a dose of 60 mg to 2400 mg, 90 mg to about 1800 mg, 120 mg to 1500 mg, 300 mg to 900 mg, 600 mg to 900 mg, 300 mg to 1200 mg, 600 mg to 1200 mg, or 900 mg to 1200 mg.

In some embodiments for the use or methods for treatment, a treatment cycle takes 21 days; 1200 mg of the anti-PD-L1 antibody is administered on the first day of each cycle and 6 mg, 8 mg, 10 mg and/or 12 mg of anlotinib is administered daily on days 1-14 of each cycle.

In some embodiments of the present application, in a three-week treatment cycle, the anti-PD-L1 antibody and anlotinib are administered to the subject in a weight ratio of (0.35-29):1, preferably (3.5-29):1, more preferably (3.5-14.5):1, most preferably (7-14.5):1, wherein the anti-PD-L1 antibody and anlotinib are administered in a single dose and multiple doses, respectively.

Pharmaceutical Composition of Anti-PD-L1 Antibody

In some embodiments of the present application, a single dose of the pharmaceutical composition of the anti-PD-L1 antibody comprises 300 mg or 600 mg of the anti-PD-L1 antibody.

In some embodiments of the present application, the pharmaceutical composition of the anti-PD-L1 antibody has a total dose of 600-2400 mg. In some embodiments, the total dose of the pharmaceutical composition of the anti-PD-L1 antibody is selected from the group consisting of 600 mg, 900 mg, 1200 mg, 1500 mg, 1800 mg, 2100 mg, 2400 mg and a range formed by any of the aforementioned values. In some embodiments, the total dose of the pharmaceutical composition of the anti-PD-L1 antibody is preferably 600-2100 mg or 900-1500 mg.

In some embodiments of the present application, the pharmaceutical composition of the anti-PD-L1 antibody comprises one or more of a buffer, an isotonicity adjusting agent, a stabilizer and/or a surfactant. In particular, the pharmaceutical composition of the anti-PD-L1 antibody comprises 1-150 mg/mL anti-PD-L1 antibody (e.g., mAb), 3-50 mM buffer, 2-150 mg/mL isotonicity adjusting agent/stabilizer, and 0.01-0.8 mg/mL surfactant, with a pH of about 4.5-6.8.

In some embodiments of the present application, for the pharmaceutical composition of the anti-PD-L1 antibody, the concentration of the anti-PD-L1 mAb is about 5-150 mg/mL, preferably about 10-60 mg/mL, more preferably about 10-30 mg/mL (w/v). In some embodiments, the concentration of the anti-PD-L1 mAb is about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, about 100 mg/mL, about 110 mg/mL or about 120 mg/mL, preferably about 10 mg/mL, about 20 mg/mL, about 30 mg/mL, about 40 mg/mL, about 50 mg/mL, or about 60 mg/mL, more preferably about 10 mg/mL, about 20 mg/mL or about 30 mg/mL (w/v). In some embodiments, the concentration of the anti-PD-L1 mAb is about 10 mg/mL (w/v). In other embodiments, the concentration of the anti-PD-L1 mAb is about 30 mg/mL (w/v). In other embodiments, the concentration of the anti-PD-L1 mAb is about 60 mg/mL (w/v).

In some embodiments of the present application, the buffer is a histidine salt buffer. The concentration of the histidine salt buffer is about 5-30 mM, preferably about 10-25 mM, more preferably about 10-20 mM, and most preferably about 10-15 mM. In some specific embodiments, the concentration of the histidine salt buffer is about 5 mM, about 10 mM, about 15 mM, about 20 mM, about 25 mM, or about 30 mM. In some embodiments, the concentration of the histidine salt buffer is about 10 mM. In other embodiments, the concentration of the histidine salt buffer is about 15 mM. In other embodiments, the concentration of the histidine salt buffer is about 20 mM. Wherein, the histidine salt buffer comprises histidine and hydrochloric acid.

In some embodiments of the present application, the isotonicity adjusting agent/stabilizer is sucrose at about 20-150 mg/mL, preferably sucrose at about 40-100 mg/mL, more preferably sucrose at about 60-80 mg/mL (w/v). In some specific embodiments, the concentration of sucrose is about 40 mg/mL, 50 mg/mL, 60 mg/mL, 70 mg/mL, 80 mg/mL, 90 mg/mL, or 100 mg/mL. In some specific embodiments, the concentration of sucrose is about 60 mg/mL. In some specific embodiments, the concentration of sucrose is about 70 mg/mL. In some specific embodiments, the concentration of sucrose is about 80 mg/mL. In some specific embodiments, the concentration of sucrose is about 90 mg/mL.

In some embodiments of the present application, the surfactant is selected from the group consisting of polysorbate 80, polysorbate 20 and poloxamer 188; preferably polysorbate 80 and polysorbate 20; and more preferably polysorbate 80. In some embodiments, the concentration of the surfactant is about 0.05-0.6 mg/mL, preferably about 0.1-0.4 mg/mL, more preferably about 0.2-0.3 mg/mL (w/v).

In some embodiments of the present application, the surfactant is polysorbate 80 or polysorbate 20 at about 0.01-0.8 mg/mL (w/v). In some specific embodiments, the surfactant is polysorbate 80 at about 0.05-0.6 mg/mL, preferably polysorbate 80 at about 0.1-0.4 mg/mL, more preferably polysorbate 80 at about 0.2-0.3 mg/mL, and most preferably polysorbate 80 at about 0.2 mg/mL. In some embodiments, the amount of polysorbate 80 in the pharmaceutical composition is about 0.1 mg/mL, 0.2 mg/mL, 0.3 mg/mL, 0.4 mg/mL, 0.5 mg/mL, or 0.6 mg/mL; preferably, the amount of polysorbate 80 in the pharmaceutical composition is about 0.2 mg/mL, 0.3 mg/mL, 0.4 mg/mL, or 0.5 mg/mL; more preferably, the amount of polysorbate 80 in the pharmaceutical composition is about 0.2 mg/mL, 0.3 mg/mL, or 0.4 mg/mL; most preferably, the amount of polysorbate 80 in the pharmaceutical composition is about 0.2 mg/mL. In some embodiments, the amount of polysorbate 80 in the pharmaceutical composition is about 0.1 mg/mL. In other embodiments, the amount of polysorbate 80 in the pharmaceutical composition is about 0.2 mg/mL. In some embodiments, the amount of polysorbate 80 in the pharmaceutical composition is about 0.3 mg/mL. In other embodiments, the amount of polysorbate 80 in the pharmaceutical composition is about 0.4 mg/mL. In some embodiments, the amount of polysorbate 80 in the pharmaceutical composition is about 0.5 mg/mL.

In some embodiments of the present application, the pH of the aqueous solution of the pharmaceutical composition is 4.0-6.8, preferably 4.5-6.5, more preferably 5.5-6.0, and most preferably 5.5. In some embodiments, the pH of the aqueous solution of the pharmaceutical composition is about 4.5, about 4.8, about 5.0, about 5.2, about 5.4, about 5.5, about 5.6, about 5.8 or about 6.0, preferably about 5.0, about 5.2, about 5.4, about 5.5 or about 5.6, and more preferably about 5.5. In some embodiments, the pH of the aqueous solution of the pharmaceutical composition is about 5.0. In some embodiments, the pH of the aqueous solution of the pharmaceutical composition is about 5.2. In some embodiments, the pH of the aqueous solution of the pharmaceutical composition is about 5.4. In some embodiments, the pH of the aqueous solution of the pharmaceutical composition is about 5.5. In some embodiments, the pH of the aqueous solution of the pharmaceutical composition is about 5.6. In some embodiments, the pH of the aqueous solution of the pharmaceutical composition is about 5.8. In some embodiments, the pH of the aqueous solution of the pharmaceutical composition is about 6.0.

In some embodiments of the present application, the pharmaceutical composition comprises: (a) an anti-PD-L1 antibody at about 20 mg/mL (w/v), (b) sucrose at about 70 mg/mL (w/v), (c) polysorbate 80 at about 0.1 mg/mL (w/v), (d) histidine at about 20 mM, and (e) optionally a suitable amount of hydrochloric acid for adjusting the pH of the composition to about 5.0. In one specific embodiment of the present application, the pharmaceutical composition comprises: (a) an anti-PD-L1 mAb at about 20 mg/mL (w/v), (b) sucrose at about 70 mg/mL (w/v), (c) polysorbate 80 at about 0.1 mg/mL (w/v), (d) histidine at about 20 mM, and (e) optionally a suitable amount of hydrochloric acid for adjusting the pH of the composition to about 5.0.

In another specific embodiment of the present application, the pharmaceutical composition comprises: (a) an anti-PD-L1 antibody at about 10 mg/mL (w/v), (b) sucrose at about 80 mg/mL (w/v), (c) polysorbate 80 at about 0.2 mg/mL (w/v), (d) histidine at about 10 mM, and (e) optionally a suitable amount of hydrochloric acid for adjusting the pH of the composition to about 5.5.

In another specific embodiment of the present application, the pharmaceutical composition comprises: (a) an anti-PD-L1 antibody at about 50 mg/mL (w/v), (b) sucrose at about 80 mg/mL (w/v), (c) polysorbate 80 at about 0.3 mg/mL (w/v), (d) histidine at about 10 mM, and (e) optionally a suitable amount of hydrochloric acid for adjusting the pH of the composition to about 5.5.

In another specific embodiment of the present application, the pharmaceutical composition comprises: (a) an anti-PD-L1 antibody at about 100 mg/mL (w/v), (b) sucrose at about 80 mg/mL (w/v), (c) polysorbate 80 at about 0.5 mg/mL (w/v), (d) histidine at about 10 mM, and (e) optionally a suitable amount of hydrochloric acid for adjusting the pH of the composition to about 5.5.

In another specific embodiment of the present application, the pharmaceutical composition comprises: (a) an anti-PD-L1 antibody at about 30 mg/mL (w/v), (b) sucrose at about 80 mg/mL (w/v), (c) polysorbate 80 at about 0.2 mg/mL (w/v), (d) histidine at about 10 mM, and (e) optionally a suitable amount of hydrochloric acid for adjusting the pH of the composition to about 5.5.

In another specific embodiment of the present application, the pharmaceutical composition comprises: (a) an anti-PD-L1 antibody at about 60 mg/mL (w/v), (b) sucrose at about 80 mg/mL (w/v), (c) polysorbate 80 at about 0.2 mg/mL (w/v), (d) histidine at about 10 mM, and (e) optionally a suitable amount of hydrochloric acid for adjusting the pH of the composition to about 5.5.

In another specific embodiment of the present application, the pharmaceutical composition comprises: (a) an anti-PD-L1 antibody at about 10 mg/mL (w/v), (b) sucrose at about 70 mg/mL (w/v), (c) polysorbate 80 at about 0.4 mg/mL (w/v), (d) histidine at about 20 mM, and (e) optionally a suitable amount of acetic acid for adjusting the pH of the composition to about 6.5.

In another specific embodiment of the present application, the pharmaceutical composition comprises: (a) an anti-PD-L1 mAb at about 10 mg/mL (w/v), (b) sucrose at about 80 mg/mL (w/v), (c) polysorbate 80 at about 0.2 mg/mL (w/v), (d) histidine at about 20 mM, and (e) optionally a suitable amount of hydrochloric acid for adjusting the pH of the composition to about 5.5.

In another specific embodiment of the present application, the pharmaceutical composition is a water-soluble injection, including but not limited to a water-soluble formulation without lyophilization or a water-soluble formulation reconstituted from a lyophilized powder. In other embodiments, the pharmaceutical composition is a lyophilized formulation. The lyophilized formulation refers to a formulation prepared by subjecting an aqueous solution to a lyophilization process in which a substance is first frozen, and then the amount of a solvent is reduced by sublimation (primary drying process) and then by desorption (secondary drying process) until the amount of the solvent is reduced to a value that no longer supports a biological activity or a chemical reaction. The lyophilized formulations of the present application can also be dried by other methods known in the art, such as spray drying and bubble drying.

Pharmaceutical Composition of Anlotinib

In some embodiments of the present application, the single dose of the pharmaceutical composition of anlotinib comprises 6 mg, 8 mg, 10 mg or 12 mg of anlotinib.

In some embodiments of the present application, according to a cycle of 2-week treatment plus 1-week interruption, the total dose of the pharmaceutical composition of anlotinib administered per treatment cycle includes 84-168 mg. In some embodiments, the total dose of the pharmaceutical composition of anlotinib includes an amount selected from the group consisting of 84 mg, 112 mg, 140 mg, 168 mg and a range formed by any of the aforementioned values. In some embodiments, the total dose of the pharmaceutical composition of anlotinib preferably comprises 112-168 mg.

Anti-PD-L1 Antibody

In some embodiments of the present application, the anti-PD-L1 antibody is the antibody disclosed in WO2016022630 or CN107001463A.

In some embodiments of the present application, the anti-PD-L1 antibody comprises an amino acid sequence as follows: a heavy chain CDR1 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 1 or SEQ ID NO: 4; a heavy chain CDR2 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 2 or SEQ ID NO: 5; a heavy chain CDR3 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 3 or SEQ ID NO: 6; a light chain CDR1 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 7 or SEQ ID NO: 10; a light chain CDR2 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 8 or SEQ ID NO: 11; and a light chain CDR3 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 9 or SEQ ID NO: 12.

In some embodiments of the present application, the anti-PD-L1 antibody comprises an amino acid sequence as follows: a heavy chain CDR1 region selected from the group consisting of SEQ ID NO: 1 and SEQ ID NO: 4; a heavy chain CDR2 region selected from the group consisting of SEQ ID NO: 2 and SEQ ID NO: 5; a heavy chain CDR3 region selected from the group consisting of SEQ ID NO: 3 and SEQ ID NO: 6; a light chain CDR1 region selected from the group consisting of SEQ ID NO: 7 and SEQ ID NO: 10; a light chain CDR2 region selected from the group consisting of SEQ ID NO: 8 and SEQ ID NO: 11; and a light chain CDR3 region selected from the group consisting of SEQ ID NO: 9 and SEQ ID NO: 12.

In some embodiments of the present application, an isolated anti-PD-L1 antibody described herein comprises: a heavy chain CDR1 region having an amino acid sequence set forth in SEQ ID NO: 1, a heavy chain CDR2 region having an amino acid sequence set forth in SEQ ID NO: 2, and a heavy chain CDR3 region having an amino acid sequence set forth in SEQ ID NO: 3; and a light chain CDR1 region having an amino acid sequence set forth in SEQ ID NO: 7, a light chain CDR2 region having an amino acid sequence set forth in SEQ ID NO: 8, and a light chain CDR3 region having an amino acid sequence set forth in SEQ ID NO: 9.

Each of the CDR regions described herein and the variants thereof described above are capable of specifically recognizing and binding to PD-L1, thereby effectively blocking the signaling between PD-L1 and PD-1.

In some embodiments of the present application, the anti-PD-L1 antibody comprises: a heavy chain variable region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 13 or SEQ ID NO: 14; and a light chain variable region having at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) homology to an amino acid sequence set forth in SEQ ID NO: 15 or SEQ ID NO: 16.

In some embodiments of the present application, the anti-PD-L1 antibody comprises: a heavy chain variable region set forth in SEQ ID NO: 13; and a light chain variable region set forth in SEQ ID NO: 15.

In some embodiments of the present application, the anti-PD-L1 antibody comprises: a heavy chain variable region set forth in SEQ ID NO: 14; and a light chain variable region set forth in SEQ ID NO: 16.

In some embodiments of the present application, the anti-PD-L1 antibody comprises: a heavy chain amino acid sequence set forth in SEQ ID NO: 17; and a light chain amino acid sequence set forth in SEQ ID NO: 18.

In some embodiments of the present application, the anti-PD-L1 antibody comprises: a heavy chain variable region set forth in SEQ ID NO: 19; and a light chain variable region set forth in SEQ ID NO: 20.

In some embodiments of the present application, the anti-PD-L1 antibody comprises: a heavy chain variable region set forth in SEQ ID NO: 21; and a light chain variable region set forth in SEQ ID NO: 18.

In one specific embodiment, the humanized anti-PD-L1 mAb disclosed herein comprises one or more conservatively substituted variants selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21. The humanized anti-PD-L1 mAb comprising the conservatively substituted variants retains the ability to specifically recognize and bind to PD-L1.

In some embodiments of the present application, the anti-PD-L1 antibody may be an IgG1 or IgG4 antibody.

In some embodiments of the present application, the anti-PD-L1 antibody is an IgG1 antibody. In some embodiments, the anti-PD-L1 antibody is a glycosylated IgG1 antibody.

In some embodiments of the present application, the anti-PD-L1 antibody comprises heavy chain complementarity determining regions (CDRs) selected from the group consisting of heavy chain CDRs derived from 13C5 and 5G11 antibodies, and light chain CDRs selected from the group consisting of light chain CDRs derived from 13C5 and 5G11 antibodies. In one embodiment, the anti-PD-L1 antibody disclosed herein comprises: a heavy chain variable region selected from the group consisting of heavy chain variable regions of ch5G11-hIgG1, ch5G11-hIgG4, ch13C5-hIgG1 and ch13C5-hIgG4 chimeric antibodies; and a light chain variable region selected from the group consisting of light chain variable regions of ch5G11-hIgG1, ch5G11-hIgG4, ch13C5-hIgG1 and ch13C5-hIgG4 chimeric antibodies. In one embodiment, the anti-PD-L1 antibody disclosed herein comprises: a heavy chain variable region selected from the group consisting of heavy chain variable regions of hu13C5-hIgG1, hu13C5-hIgG4, hu5G11-hIgG1 and hu5G11-hIgG4 humanized antibodies; and a light chain variable region selected from the group consisting of light chain variable regions of hu13C5-hIgG1, hu13C5-hIgG4, hu5G11-hIgG1 and hu5G11-hIgG4 humanized antibodies. Reference may be made to the description of Patent No. WO2016022630 or CN107001463A: 13C5, ch13C5-hIgG1, ch13C5-hIgG4, hu13C5-hIgG1 or hu13C5-hIgG4 has an HCDR1 sequence of SYGMS (SEQ ID NO: 4), an HCDR2 sequence of SISSGGSTYYPDSVKG (SEQ ID NO: 5), an HCDR3 sequence of GYDSGFAY (SEQ ID NO: 6), an LCDR1 sequence of ASQSVSTSSSSFMH (SEQ ID NO: 10), an LCDR2 sequence of YASNLES (SEQ ID NO: 11), and an LCDR3 sequence of QHSWEIPYT (SEQ ID NO: 12); 5G11, ch5G11-hIgG1, ch5G11-hIgG4, hu5G11-hIgG1 or hu5G11-hIgG4 has an HCDR1 sequence of TYGVH (SEQ ID NO: 1), an HCDR2 sequence of VIWRGVTTDYNAAFMS (SEQ ID NO: 2), an HCDR3 sequence of LGFYAMDY (SEQ ID NO: 3), an LCDR1 sequence of KASQSVSNDVA (SEQ ID NO: 7), an LCDR2 sequence of YAANRYT (SEQ ID NO: 8), and an LCDR3 sequence of QQDYTSPYT (SEQ ID NO: 9).

In some embodiments of the present application, the anti-PD-L1 antibody in the pharmaceutical combination may be selected from one or more. As used herein, the term "more" refers to more than one, for example, two, three, four, five or more. For example, in some embodiments of the present application, the anti-PD-L1 antibody is selected from the group consisting of an antibody comprising a heavy chain variable region set forth in SEQ ID NO: 13 and a light chain variable region set forth in SEQ ID NO: 15, or selected from the group consisting of an antibody comprising a heavy chain variable region set forth in SEQ ID NO: 14 and a light chain variable region set forth in SEQ ID NO: 16, or selected from the group consisting of a combination thereof. As another example, the anti-PD-L1 antibody is selected from the group consisting of an antibody comprising a heavy chain amino acid sequence set forth in SEQ ID NO: 17 and a light chain amino acid sequence set forth in SEQ ID NO: 18, or selected from the group consisting of an antibody comprising a heavy chain amino acid sequence set forth in SEQ ID NO: 19 and a light chain amino acid sequence set forth in SEQ ID NO: 20, or selected from the group consisting of an antibody comprising a heavy chain amino acid sequence set forth in SEQ ID NO: 21 and a light chain amino acid sequence set forth in SEQ ID NO: 18, or selected from the group consisting of combinations of any of the foregoing.

Anlotinib

As used herein, the chemical name of the free base of anlotinib is 1-[[[4-(4-fluoro-2-methyl-1H-indol-5-yl) oxy-6-methoxyquinolin-7-yl]oxy]methyl]cyclopropylamine, which has the following structural formula:

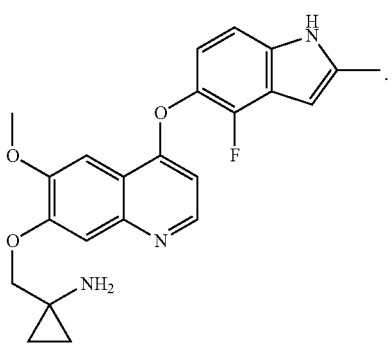

As used herein, the anlotinib includes non-salt forms thereof (for example, free bases) and further includes pharmaceutically acceptable salts thereof. All the non-salt forms or salts fall within the scope of protection of the present application. For example, the pharmaceutically acceptable salt of anlotinib can be hydrochloride or dihydrochloride. Unless otherwise stated, the dose of anlotinib or a salt thereof involved in present application is calculated based on the molecular weight of anlotinib.

Tumor in Biliary System

In some embodiments of the present application, the tumor in biliary system is an adenocarcinoma in biliary system. In some embodiments of the present application, the tumor in biliary system includes gallbladder cancer (GBC), intrahepatic cholangiocarcinoma (IHCC), and extrahepatic cholangiocarcinoma (EHCC). In some embodiments of the present application, the extrahepatic cholangiocarcinoma includes perihilar cholangiocarcinoma (hilar cholangiocarcinoma, also known as Klatskin tumor) and distal bile duct cancer (distal cholangiocarcinoma). In some embodiments of the present application, the tumor in biliary system includes adenocarcinoma-type gallbladder carcinoma, adenocarcinoma-type intrahepatic cholangiocarcinoma, or adenocarcinoma-type extrahepatic cholangiocarcinoma.

In some embodiments of the present application, the tumor in biliary system includes unresectable, advanced, or metastatic tumors in biliary system. In some embodiments of the present application, the tumor in biliary system includes unresectable, advanced or metastatic adenocarcinoma-type gallbladder adenocarcinomas, adenocarcinoma-type intrahepatic cholangiocarcinoma, and adenocarcinoma-type extrahepatic cholangiocarcinoma. In some embodiments of the present application, the patient with the tumor in biliary system has failed previous chemotherapy. In some embodiments of the present application, the patient with the tumor in biliary system has failed previous first-line chemotherapy.

Liver Cancer

In some embodiments of the present application, the liver cancer is hepatocellular carcinoma (HCC). In some embodiments of the present application, the liver cancer is primary hepatocellular carcinoma. In some embodiments of the present application, the liver cancer is selected from the group consisting of advanced and/or metastatic hepatocellular carcinomas. In some embodiments, the liver cancer is an unresectable hepatocellular carcinoma. In some embodiments, the liver cancer is a hepatocellular carcinoma that has failed previous local treatment or is not suitable for local treatment including, but not limited to, ablation (including, but not limited to, radiofrequency ablation, cryoablation, percutaneous ethanol injection therapy and microwave ablation), radiation therapy, and/or hepatic arterial infusion chemotherapy. In some embodiments, the liver cancer is a liver cancer that has failed sorafenib and/or lenvatinib treatment.

Triple Negative Breast Cancer

In some embodiments of the present application, the subject with triple negative breast cancer has received surgery, chemotherapy, and/or radiation therapy. In some specific embodiments, the subject with triple negative breast cancer has previously received a first-line chemotherapy. In some specific embodiments, the subject with triple negative breast cancer has received anthracycline and/or taxane medications. In some specific embodiments, the subject with triple negative breast cancer at least has received a first-line systemic therapy and received an anthracycline and/or taxane.

Lung Cancer

In some embodiments of the present application, the lung cancer is non-small cell lung cancer. In some embodiments, the lung cancer includes squamous lung carcinoma or lung adenocarcinoma. In some embodiments, the lung cancer is advanced lung cancer. In some embodiments, the lung cancer is EGFR or ALK wild-type non-small cell lung cancer. In some embodiments, the lung cancer is selected from the group consisting of advanced squamous non-small cell lung cancer and advanced adenocarcinoma non-small cell lung cancer. In some embodiments, the lung cancer is selected from EGFR or ALK wild-type squamous non-small cell lung cancer, and EGFR or ALK wild-type adenocarcinoma non-small cell lung cancer. In some embodiments, the lung cancer is BRaf or EGFR mutant non-small cell lung cancer, e.g., BRAF p.V600E, EGFR del and/or EGFR-T790M non-small cell lung cancer.

In some embodiments, the lung cancer patient has previously received chemotherapy; in some embodiments, the lung cancer is advanced (stage IIIB and/or IV) lung cancer that has failed or is intolerant to a first-line standard chemotherapy.

As used herein, the chemotherapy includes, but is not limited to, one or more of platinum-based drugs, fluoropyrimidine derivatives, camptothecins, taxanes, vinblastines, anthracyclines, antibiotics, podophyllums, antitumor drugs, and antimetabolites; and examples that may be listed include, but are not limited to: one or more of platinum-based drugs (e.g., oxaliplatin, cisplatin, carboplatin, nedaplatin, and dicycloplatin), fluoropyrimidine derivatives (e.g., gemcitabine, capecitabine, ancitabine, fluorouracil, difuradin, doxifluidine, tegafur, carmofur, and trifluridine), taxanes (e.g., paclitaxel, albumin-bound paclitaxel, and docetaxel), camptothecin and analogs thereof (e.g., camptothecin, hydroxycamptothecin, 9-aminocamptothecin, 7-ethyl-camptothecin, irinotecan, topotecan), vinca alkaloids (vinorelbine, vinblastine, vincristine, vindesine, vinflunine), anthracyclines (epirubicin, doxombicin, daunorubicin, pirarubicin, amrubicin, idarubicin, mitoxantrone, aclarubicin, valrubicin, zorubicin, pixantrone), pemetrexed, carmustine, melphalan, etoposide, teniposide, mitomycin, Ifosfamide, cyclophosphamide, azacitidine, methotrexate, bendamustine, liposomal doxombicin, actinomycin D (dactinomycin), bleomycin, pingyangmycin, temozolomide, dacarbazine, peplomycin, eribulin, plinabulin, sapacitabine, treosulfan, 153Sm-EDTMP, tegafur-gimeracil-oteracil potassium, and encequidar.

Administration

The content below is not intended to limit the manner of administration of the pharmaceutical combination disclosed herein.

The components in the pharmaceutical composition disclosed herein can be administered independently, or some or all of the components are co-administered in various proper routes including, but not limited to, oral administration or parenteral administration (by intravenous, intramuscular, local or subcutaneous routes). In some embodiments, the components in the pharmaceutical combination disclosed herein can be administered independently, or some or all of the components are co-administered by means of oral administration or injection, for example, intravenous injection or intraperitoneal injection.

The components in the pharmaceutical composition disclosed herein can be formulated independently in suitable dosage forms, or some or all of the components are co-formulated in a suitable dosage form including, but not limited to, tablet, lozenge, pill, capsule (for example, hard capsule, soft capsule, enteric capsule and microcapsule), elixir, granule, syrup, injection (intramuscular, intravenous and intraperitoneal), granule, emulsion, suspension, solution, dispersant and dosage forms of sustained-released preparations for oral or non-oral administration.

The components in the pharmaceutical combination disclosed herein can be formulated independently, or some or all of the components are co-formulated with a pharmaceutically acceptable carrier and/or excipient.

The pharmaceutical combination disclosed herein may further comprise an additional therapeutic agent. In one embodiment, the additional therapeutic agent can be a known cancer therapeutic agent in the art.

Technical Effects

Generally, use of the combined pharmaceutical composition disclosed herein will provide:
(1) better efficacy in controlling tumor growth or even eliminating tumors as compared with either drug of the combination administered alone;
(2) fewer doses as compared with either drug of the combination administered alone;
(3) good tolerability in subjects, and fewer adverse effects and/or complications as compared with either drug administered alone;
(4) a higher disease control rate in patients treated;
(5) longer survivals (e.g., median survival, progression-free survival, or overall survival) in patients treated;
(6) longer survivals (e.g., median survival, progression-free survival, or overall survival) in patients treated as compared with standard chemotherapies;
(7) a longer duration of response (DOR); and/or
(8) better activity in treating a tumor in biliary system, liver cancer, triple negative breast cancer and/or lung cancer and better anti-tumor synergistic effect, as compared with either drug of the combination administered alone.

Definitions and Description

Unless otherwise stated, the following terms used in the present application shall have the following meanings. A specific term, unless otherwise specifically defined, should not be considered uncertain or unclear, but construed according to its common meaning in the art. When referring to a trade name, it is intended to refer to its corresponding commercial product or its active ingredient.

As used herein, the term "combined pharmaceutical composition" refers to a combination of two or more active ingredients (administered as the respective active ingredients themselves, or as their respective pharmaceutically acceptable salts or esters, derivatives, prodrugs, or compositions) that are administered simultaneously or sequentially. The terms "combined pharmaceutical composition", "pharmaceutical composition" and "pharmaceutical combination" are used interchangeably herein.

As used herein, the term "antibody" refers to a binding protein having at least one antigen-binding domain. The antibody and the fragment thereof disclosed herein can be an intact antibody or any fragment thereof. Thus, the antibody and the fragment thereof disclosed herein include a monoclonal antibody or a fragment thereof and an antibody variant or a fragment thereof, as well as an immunoconjugate. Examples of the antibody fragment include a Fab fragment, a Fab' fragment, an F(ab')$_2$ fragment, an Fv fragment, an isolated CDR region, a single chain Fv molecule (scFv), an Fd fragment and other antibody fragments known in the art. The antibody and the fragment thereof may also include a recombinant polypeptide, a fusion protein, and a bispecific antibody. The anti-PD-L1 antibody and the fragment thereof disclosed herein can be of IgG1, IgG2, IgG3, or IgG4 isotype. The term "isotype" refers to the class of antibodies encoded by the heavy chain constant region gene. In one embodiment, the anti-PD-L1 antibody and the fragment thereof disclosed herein are of the IgG1 or IgG4 isotype. The anti-PD-L1 antibody and the fragment thereof of the present application can be derived from any species including, but not limited to, mouse, rat, rabbit, primate, llama, and human. The anti-PD-L1 antibody and the fragment thereof can be a chimeric antibody, a humanized antibody or an intact human antibody. In one embodiment, the anti-PD-L1 antibody is an antibody produced by a hybridoma cell line derived from a mouse. Thus, in one embodiment, the anti-PD-L1 antibody is a murine antibody. In another embodiment, the anti-PD-L1 antibody is a chimeric antibody. In another embodiment, the chimeric antibody is a mouse-human chimeric antibody. In another embodiment, the antibody is a humanized antibody. In another embodiment, the antibody is derived from a murine antibody and is humanized.

The term "humanized antibody" refers to an antibody comprising complementarity determining regions (CDRs) derived from a non-human antibody, and framework and constant regions derived from a human antibody. For example, an anti-PD-L1 antibody disclosed herein may comprise CDRs derived from one or more murine antibodies as well as human framework and constant regions. Thus, in one embodiment, the humanized antibody disclosed herein binds to the same epitope on PD-L1 as the murine antibody from which the CDRs of the humanized antibody are derived. Exemplary humanized antibodies are disclosed herein. Additional anti-PD-L1 antibodies or variants thereof comprising the heavy and light chain CDRs disclosed herein can be generated using any human framework sequences, and are also included in the present application. In one embodiment, framework sequences suitable for use in the present application include those similar in structure to the framework sequences disclosed herein. Additional modifications may be made in the framework regions to improve the properties of the antibodies disclosed herein. Such additional framework modifications may include: chemical modifications, point mutations for reducing immunogenicity or removing T cell epitopes, or modifications reverting the mutations to residues in original germline sequences. In some embodiments, such modifications include those corresponding to the mutations exemplified herein, including reversions to germline sequences. For example, in one embodiment, one or more amino acids in the human VH and/or VL framework regions of the humanized antibodies disclosed herein are reverted to the corresponding amino acids in the parent murine antibodies. For example, for the VH and VL of humanized 5G11 and humanized 13C5 antibodies, several sites of framework amino acids of the template human antibodies described above may be reverted to the corresponding amino acid sequences in the mouse 5G11 and 13C5 antibodies. In one embodiment, the amino acids at positions 53, 60 and/or 67 of the light chain variable region are reverted to the corresponding amino acids found at the positions in mouse 5G11 or 13C5 light chain variable region. In another embodiment, the amino acids at positions 24, 28, 30, 49, 73, 83 and/or 94 of the heavy chain variable region are reverted to the corresponding amino acids found at the positions in mouse 5G11 or 13C5 heavy chain variable region. In one embodiment, the humanized 5G11 antibody comprises: a light chain variable region, wherein the amino acid at position 60 is mutated from Ser (S) to Asp (D) and the amino acid at position 67 is mutated from Ser (S) to Tyr (Y); and a heavy chain variable region, wherein the amino acid at position 24 is mutated from Phe (F) to Val (V), the amino acid at position 49 is mutated from Ala (A) to Gly (G), the amino acid at position 73 is mutated from Thr (T) to Asn (N), and the amino acid at position 83 is mutated from Thr (T) to Asn (N). In one embodiment, the humanized 13C5 antibody comprises: a light chain variable region, wherein the amino acid at position 53 is mutated from Tyr (Y) to Lys (K); and a heavy chain variable region, wherein the amino acid at position 28 is mutated from Thr (T) to Ile (I), the amino acid at position 30 is mutated from Ser (S) to Arg (R), the amino acid at position 49 is mutated from Ser (S) to Ala (A), and the amino acid at position 94 is mutated from Tyr (Y) to Asp (D). Additional or alternative reverse mutations can be made in the framework regions of the humanized antibodies disclosed herein to improve the properties of the antibodies. The present application also includes humanized antibodies that bind to PD-L1 and comprise framework modifications corresponding to the exemplary modifications disclosed herein relative to any suitable framework sequence, as well as other framework modifications that otherwise improve antibody properties.

The present application provides an isolated antibody or fragment thereof that binds to PD-L1, wherein the antibody can be produced by a hybridoma selected from the group consisting of the hybridomas designated herein as 13C5 and 5G11. Accordingly, the present application also includes hybridomas 13C5 and 5G11, and any hybridomas that produce the antibodies disclosed herein. The present application also provides isolated polynucleotides encoding the antibodies and fragments thereof disclosed herein. The present application also includes expression vectors comprising the isolated polynucleotides, and host cells comprising the expression vectors.

The term "isolated antibody" refers to an antibody that is substantially free of other antibodies having different antigenic specificities (e.g., an isolated antibody that specifically binds to PD-1 is substantially free of antibodies that specifically bind to antigens apart from PD-1). However, an isolated antibody that specifically binds to PD-1 may have cross-reactivity with other antigens (such as PD-1 molecules from different species). Furthermore, the isolated antibody may be substantially free of other cellular materials and/or chemicals.

The term "monoclonal antibody" ("mAb") refers to a non-naturally occurring preparation of antibody molecules of an individual molecule component (i.e., antibody molecules whose base sequences are substantially identical and which exhibit a single binding specificity and affinity for a particular epitope). mAb is an example of the isolated antibody. mAbs can be produced by hybridoma techniques, recombinant techniques, transgenic techniques, or other techniques known to those of skill in the art.

The antibody or antigen binding fragment thereof disclosed herein is specific for PD-L1. In one embodiment, the antibody or fragment thereof is specific for PD-L1. In one embodiment, the antibody or fragment thereof disclosed herein binds to human or primate PD-L1, but does not bind to PD-L1 from any other mammal. In another embodiment, the antibody or fragment thereof does not bind to mouse PD-L1. The terms "human PD-L1", "hPD-L1", "huPD-L1" and the like, are used interchangeably herein and refer to human PD-L1 and variants or isotypes of human PD-L1. The terms "specific", "specificity" and "specifically" refer to that the antibody or fragment thereof binds to PD-L1 with greater affinity than any other targets.

The terms "treat" and "treatment" usually refer to acquiring needed pharmacological effect and/or physiological effect. In terms of partially or fully stabilizing or curing the disease and/or a side effect of the disease, the effect can be therapeutic. As used herein, "treat" and "treatment" encompass any treatment to a disease in a patient, including (a) inhibiting a symptom of a disease, i.e., blocking the progression of the disease; or (b) alleviating a symptom of a disease, i.e., causing remission of the disease or the symptom.

The term "effective amount" refers to an amount of the compound disclosed herein for (i) treating a specific disease, condition or disorder; (ii) alleviating, improving or eliminating one or more symptoms of a specific disease, condition or disorder, or (iii) preventing or delaying onset of one or more symptoms of a specific disease, condition or disorder described herein. The amount of active substance (e.g., an antibody or compound disclosed herein) constituting a "therapeutically effective amount" may vary according to factors such as the disease state, age, sex, and weight of the individual, and the ability of a therapeutic agent or a combination of therapeutic agents to elicit a desired response in the individual. The effective amount may also be determined routinely by those skilled in the art in accordance with their knowledge and the present disclosure.

The terms "administer" and "administration" refer to physically introducing the composition comprising the therapeutic agent to the entity using any of a variety of methods and delivery systems known to those skilled in the art. Routes of administration of immune checkpoint inhibitors (e.g., an anti-PD-1 antibody or an anti-PD-L1 antibody) include intravenous, intramuscular, subcutaneous, intraperitoneal, spinal, or other parenteral routes of administration, for example, by injection or infusion. As used herein, the phrase "parenteral administration" refers to routes of administration apart from enteral and local administrations, typically by injection, including, but not limited to, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and infrasternal injection and infusion and in vivo electroporation. In some embodiments, the immune checkpoint inhibitor (e.g., an anti-PD-1 antibody or an anti-PD-L1 antibody) is administered by a non-parenteral route, and in some embodiments, by oral administration. Other non-parenteral routes include local, epidermal or mucosal routes of administration, for example, intranasal, vaginal, rectal, sublingual or local administration. Administration may also be performed, e.g., once, multiple times, and/or over one or more extended periods of time.

The term "dose" refers to a dose administered to a patient without considering the weight or the body surface area (BSA) of the patient. For example, a 60 kg human and a 100 kg human will receive the same dose of antibody (e.g., 240 mg of anti-PD-1 antibody).

The term "weight-based dose" as used herein refers to a dose administered to a patient calculated on the basis of the patient's body weight. For example, when a patient having a weight of 60 kg requires 3 mg/kg of anti-PD-1 antibody, one can extract an appropriate amount of anti-PD-1 antibody (i.e., 180 mg) at a time from a fixed-dose formulation of the anti-PD-1 antibody.

Anlotinib can be administered in various routes including, but not limited to, oral, parenteral, intraperitoneal, intravenous, intra-arterial, transdermal, sublingual, intramuscular, rectal, transbuccal, intranasal, inhalational, vaginal, intraocular, topical, subcutaneous, intralipid, intra-articular and intrathecal administrations. In some specific embodiments, the drug is administered orally. The amount of anlotinib administered can be determined according to the severity of the disease, the response of the disease, any treatment-related toxicity, and the age and health of a patient. For example, the daily dose of anlotinib can be 2 mg to 20 mg. In some embodiments, the daily dose of anlotinib or the pharmaceutically acceptable salt thereof can be 2 mg, 3 mg, 4 mg, 5 mg, 6 mg, 7 mg, 8 mg, 9 mg, 10 mg, 11 mg, 12 mg, 13 mg, 14 mg, 15 mg and 16 mg. Anlotinib can be administered once or multiple times daily. In one embodiment, anlotinib is administered once daily in the form of a solid oral preparation.

The regimen of anlotinib can be determined comprehensively depending on the activity and toxicity of the medicament, tolerance of the patient, etc. Preferably, anlotinib is administered at intervals Administration at intervals comprises a treatment period and an interruption period. In the treatment period, anlotinib can be administered once or multiple times daily. For example, the ratio of the treatment period to the interruption period in days is 2:0.5-2:5, preferably 2:0.5-2:3, more preferably 2:0.5-2:2, and most preferably 2:0.5-2:1. In some embodiments, the treatment is administered for 2 weeks and interrupted for 2 weeks. In some embodiments, the treatment is administered for 2 weeks and interrupted for 1 week. In some embodiments, the treatment is administered for 5 days and interrupted for 2 days. For example, anlotinib can be administered once daily at a dose of 6 mg, 8 mg, 10 mg or 12 mg for 2 weeks, and interrupted for 1 week.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" includes salts formed by basic radicals and free acids and salts formed by acidic radicals and free bases, for example, hydrochloride, hydrobromide, nitrate, sulfate, phosphate, formate, acetate, trifluoroacetate, fumarate, oxalate, maleate, citrate, succinate, mesylate, benzenesulfonate and p-methylbenzenesulfonate, preferably, hydrochloride, hydrobromide, sulfate, formate, acetate, trifluoroacetate, fumarate, maleate, mesylate, p-methylbenzenesulfonate, sodium salt, potassium salt, ammonium salt, and amino acid salt. In the present application, when forming a pharmaceutically acceptable salt, the free acid and the basic radical are in a molar ratio of about 1:0.5 to 1:5, preferably 1:0.5, 1:1, 1:2, 1:3, 1:4, 1:5, 1:6, 1:7 or 1:8.

The terms "subject" and "patient" are used interchangeably herein. In some embodiments, the term "subject" or "patient" refers to a mammal. In some embodiments, the subject or patient is a mouse. In some embodiments, the subject or patient is a human.

The term "about" shall be understood to include a range of three standard deviations from the mean value or a standard tolerance range in a specific field. In some embodiments, the term "about" shall be understood as a variation not exceeding 0.5 The term "about" modifies all listed values thereafter. For example, "about 1, 2 and 3" means "about 1", "about 2", and "about 3".

As used herein, "combined use" or "use in combination" means that two or more active substances may be administered to a subject simultaneously or sequentially in any order as a single formulation.

The term "single dose" refers to the smallest unit of packaging containing a certain quantity of pharmaceutical product, for example, in a box of seven capsules, each capsule is a single dose; or a vial of injection can be a single dose. As used herein, the terms "single dose" and "unit dose" have the same meaning and are used interchangeably.

The term "multiple dose" consists of multiple single doses.

The term "pharmaceutical composition" refers to a mixture consisting of one or more of the active ingredients or pharmaceutical combinations thereof disclosed herein and a pharmaceutically acceptable excipient. The pharmaceutical composition is intended to facilitate the administration of the compound or the pharmaceutical combination thereof to a subject.

As used herein, unless otherwise stated, the terms "comprise", "comprises" and "comprising" or equivalents thereof are open-ended statements and mean that elements, components and steps that are not specified may be included in addition to those listed.

All patents, patent applications and other identified publications are expressly incorporated herein by reference for the purpose of description and disclosure. These publications are provided solely because they were disclosed prior to the filing date of the present application. All statements as to the dates of these documents or description as to the contents of these documents are based on the information available to the applicant and do not constitute any admission as to the correctness of the dates of these documents or the contents of these documents. Moreover, in any country or region, any reference to these publications herein is not to be construed as an admission that the publications form part of the commonly recognized knowledge in the art.

DETAILED DESCRIPTION

For clarity, the present application is further described with the following examples, which are, however, not intended to limit the scope of the present application. All reagents used in the present application are commercially available and can be used without further purification. In the examples, the anti-PD-L1 antibody was prepared as described in WO2016022630, and after affinity chromatography, the antibody-containing eluate was obtained by conventional antibody purification methods.

Example 1. Clinical Trial of Tumor in Biliary System 1.1 Inclusion Criteria
1) Aged≥18 years; ECOG physical condition: 0-1; an expected survival of more than 3 months;
2) Histologically or pathologically confirmed patients with unrescetable or metastatic biliary tract cancer include intrahepatic cholangiocarcinoma (IHCC), extrahepatic cholangiocarcinoma (EHCC), and gallbladder cancer (GBC);
3) Having at least one measurable lesion (RECIST 1.1);
4) Previous first-line chemotherapy failure. Chemotherapy failure refers to: disease progression during the treatment or after the last treatment; or cannot be tolerated during the treatment due to toxic and side effects;
5) Laboratory tests should meet the follows: blood routine examination: hemoglobin (Hb)≥80 g/L (no blood transfusion within 14 days), absolute neutrophil count (ANC)≥1.5×10$^9$/L and platelet (PLT)≥75×10$^9$/L; biochemical tests: alanine transaminase (ALT) and aspartate transaminase (AST)≤2.5×ULN (for patients with liver metastasis, ≤5×ULN), serum total bilirubin (TBIL)≤2×ULN (for patients with Gilbert syndrome, ≤3×ULN), serum creatinine (Cr)≤1.5×ULN and creatinine clearance rate>50 μmon; blood coagulation function: activated partial thromboplastin time (APTT), international normalized ratio (INR) and prothrombin time (PT)≤1.5×ULN; doppler ultrasound evaluation: left ventricular ejection fraction (LVEF)≥50%;
6) Female subjects should agree to take contraceptive measures (such as intrauterine devices [IUD], contraceptives or condoms) during the study and for 6 months after the study; serum or urine pregnancy test results should be negative within 7 days before enrollment, and the subjects must not be breastfeeding; male subjects should agree to take contraceptive measures during the study and for 6 months after the study; and
7) Voluntary participation, written informed consent and good compliance.

1.2 Test Drug

Anti-PD-L1 antibody hu5G11-hIgG1 injection: 1200 mg of anti-PD-L1 antibody injection (100 mg/10 mL) was diluted to 250 mL using normal saline; the diluted drug was administered in 60±5 min by infusion; the infusion system was flushed with normal saline according to the routine requirements of hospitals after the completion of infusion; the injection was administered once every 21 days, i.e., in 21-day treatment cycles.

Anlotinib hydrochloride capsule (active ingredient: anlotinib dihydrochloride): 5 minutes before or after the start of anti-PD-L1 antibody infusion, 10 mg of anlotinib hydrochloride capsule was administered orally at fasting; the treatment was given for 2 weeks and interrupted for 1 week, i.e., in 21-day treatment cycles.

Dosage: 12 mg, 10 mg and 8 mg.

1.3 Evaluation Criteria

Disease status was assessed by RECIST 1.1/irRECIST, and mainly by RECIST 1.1 criteria.

1.4 Endpoints

Objective response rate (ORR)=(complete response (CR)+partial response (PR));

Anti-tumor efficacy endpoints: progression-free survival (PFS), disease control rate (DCR=CR+PR+ stable disease (SD)), overall survival (OS), stable disease (SD), PR (partial response), and the like.

1.5 Results

| No. | Pathological diagnosis | Lesion | Size of target lesion (baseline) | Size of target lesion (C2) | Size of target lesion (C4) | Size of target lesion (C6) | Size of target lesion (C8) | Size of target lesion (C10) |
|---|---|---|---|---|---|---|---|---|
| C01002 | Intrahepatic cholangiocarcinoma | Left retroperitoneum | 20 mm | 18 mm | 17 mm | 14 mm | 16 mm | 18 mm |
|  |  | Right hilar lymph node | 16 mm | 15 mm | 13 mm | 14 mm | 14 mm | 14 mm |
|  |  | Left lung | 10 mm | 7 mm | 6 mm | 6 mm | 6 mm | 7 mm |
|  | Sum |  | 46 mm | 40 mm SD | 36 mm SD | 34 mm SD | 36 mm SD | 39 mm SD |
| C01006 | Intrahepatic cholangiocarcinoma | Right liver lobe | 85 mm | 89 mm SD | 85 mm SD | 84 mm SD | 85 mm SD | — |
| C01007 | Intrahepatic cholangiocarcinoma | Right liver lobe | 68 mm | 62 mm | 57 mm | 57 mm | 58 mm | — |
|  |  | Liver top | 46 mm | 44 mm | 45 mm | 45 mm | 45 mm | — |
|  |  | Right lung | 13 mm | 11 mm | 10 mm | 5 mm | 5 mm | — |
|  | Sum |  | 127 mm | 117 mm SD | 112 mm SD | 107 mm SD | 108 mm SD | — |
| C01009 | Gallbladder cancer | Abdominal cavity (sum) | 58 mm | 45 mm SD | 41 mm SD | 36 mm PR | — | — |
| C01017 | Intrahepatic cholangiocarcinoma | Left liver lobe | 86 mm | 97 mm | 92 mm | 90 mm | — | — |
|  |  | Pelvic lymph node metastasis | 26 mm | 15 mm | 15 mm | 13 mm | — | — |
|  | Sum |  | 112 mm | 112 mm SD | 107 mm SD | 103 mm SD | — | — |

-continued

| No. | Pathological diagnosis | Lesion | Size of target lesion (baseline) | Size of target lesion (C2) | Size of target lesion (C4) | Size of target lesion (C6) | Size of target lesion (C8) | Size of target lesion (C10) |
|---|---|---|---|---|---|---|---|---|
| C01021 | Extrahepatic cholangiocarcinoma | Abdominal cavity | 58 mm | 58 mm | 48 mm | 48 mm | | |
| | | Right liver lobe | 27 mm | 33 mm | 26 mm | 25 mm | | |
| | | Right posterior liver lobe | 18 mm | 11 mm | 9 mm | 8 mm | | |
| | | Abdominal cavity lymph nodes | 15 mm | 23 mm | 26 mm | 25 mm | | |
| | | Sum | 118 mm | 125 mm SD | 109 mm SD | 106 mm SD | — | — |

Medication: patients C01002, C01007 and C01017 were administered with a combination of 1200 mg of anti-PD-L1 antibody hu5G11-hIgG1 injection and 10 mg of anlotinib hydrochloride capsule. Patients C01009 and C01021 were administered with a combination of 1200 mg of anti-PD-L1 antibody hu5G11-hIgG1 injection and 12 mg of anlotinib hydrochloride capsule. Patient C01006 was administered with a combination of 1200 mg of anti-PD-L1 antibody hu5G11-hIgG1 injection and 12 mg of anlotinib hydrochloride capsule, and the dose of anitinib hydrochloride capsule was later reduced to 10 mg (in examples of the present application, the amount of anlotinib hydrochloride capsule was based on the weight of anlotinib contained therein).
Patient diagnosis and previous treatment:
Patient C01002: left hemihepatectomy + hepatomegaly lymphadenectomy. Metastasis after radiotherapy and 2 cycles of DC-CIK cell treatment, and disease progression after 3 radio knife treatments and 4 cycles of GP regimen (gemcitabine + cisplatin). Patient C01006: immunohistochemistry: CA19.9(2+), CK18(3+), CK19(2+), CK7(2+) and Ki-67(+20-30%). PD after 6 cycles of albumin paclitaxel + tegafur-gimeracil-oteracil potassium capsule treatment, then PD (progression of disease) after interventional therapy.
Patient C01007: immunohistochemistry: CA19.9(2+), CD34(2+), CK18(2+), CK19(2+), CK7(2+) and Ki-67(+, 10%). Gemcitabine + capecitabine combination therapy, bone marrow suppression. Disease progression, followed by oxaliplatin + tegafur-gimeracil-oteracil potassium capsule q3w. Followed by albumin paclitaxel + apatinib.
Patient C01009: immunohistochemistry: PCX(+), CK(+), CK19(partial +), AFP(+), CD56(+) and Ki-67(+10%). Gemcitabine 1.4 g d1/8 + cisplatin 40 mg d2/3, intolerant.
Patient C01017: immunohistochemistry: CK18(3+), CK19(3+), CK7(3+), CA19.9(1+), AFP(1+) and Ki-67(+30%). The GC regimen (Gemcitabine 1.6 g d1/1.4 g d8 + tegafur-gimeracil-oteracil 60 mg bid po/3 w) was not tolerated after 4 weeks.
Patient C01021: tegafur-gimeracil-oteracil potassium + oxaliplatin combination, 6 cycles.

Example 2. Clinical Trial of Liver Cancer

2.1 Inclusion Criteria

1) Aged≥18 years; ECOG physical condition: 0-1; an expected survival of more than 3 months;
2) Histopathologically or cytologically confirmed advanced hepatocellular carcinoma (Barcelona hepatoma stage C, or stage B unsuitable for or refractory to local treatment);
3) Having at least one measurable lesion (RECIST 1.1);
4) Liver cancer patients were not treated with immunotherapy;
5) Laboratory test should meet the follows: blood routine examination: hemoglobin (Hb)≥80 g/L (no blood transfusion within 14 days), absolute neutrophil count (ANC)≥1.5×10$^9$/L and platelet (PLT)≥75×10$^9$/L; biochemical tests: alanine transaminase (ALT) and aspartate transaminase (AST)≤2.5×ULN (for patients with liver metastasis, ≤5×ULN), serum total bilirubin (TBIL)≤2×ULN (for patients with Gilbert syndrome, ≤3×ULN), serum creatinine (Cr)≤1.5×ULN and creatinine clearance rate>50 μmon; blood coagulation function: activated partial thromboplastin time (APTT), international normalized ratio (INR) and prothrombin time (PT)≤1.5×ULN; doppler ultrasound evaluation: left ventricular ejection fraction (LVEF)≥50%;
6) Female subjects should agree to take contraceptive measures (such as intrauterine devices [IUD], contraceptives or condoms) during the study and for 6 months after the study; serum or urine pregnancy test results should be negative within 7 days before enrollment, and the subjects must not be breastfeeding; male subjects should agree to take contraceptive measures during the study and for 6 months after the study; and
7) Voluntary participation, written informed consent and good compliance.

2.2 Test Drug

Anti-PD-L1 antibody hu5G11-hIgG1 injection: 1200 mg of anti-PD-L1 antibody injection (100 mg/10 mL) was diluted to 250 mL using normal saline; the diluted drug was administered in 60±5 min by infusion; the infusion system was flushed with normal saline according to the routine requirements of hospitals after the completion of infusion; the injection was administered once every 21 days.

Anlotinib hydrochloride capsule (active ingredient: anlotinib dihydrochloride): 5 minutes before or after the start of anti-PD-L1 antibody infusion, 10 mg of anlotinib hydrochloride capsule was administered orally at fasting; the treatment was given for 2 weeks and interrupted for 1 week, i.e., in 21-day treatment cycles.

Dosage: 12 mg, 10 mg and 8 mg.

2.3 Evaluation Criteria

Disease status was assessed by RECIST 1.1/irRECIST, and mainly by RECIST 1.1 criteria.

2.4 Endpoints

Objective response rate (ORR)=(complete response (CR)+partial response (PR)); Anti-tumor efficacy endpoints: progression-free survival (PFS), disease control rate (DCR=CR+PR+ stable disease (SD)), overall survival (OS), stable disease (SD), partial response (PR), and the like.

2.5 Results

| No. | Pathological diagnosis | Lesion | Size of target lesion (baseline) | Size of target lesion (C2) | Size of target lesion (C4) | Size of target lesion (C6) | Size of target lesion (C8) | Size of target lesion (C10) |
|---|---|---|---|---|---|---|---|---|
| C01003 | Liver cancer | Node in upper lobe of left lung | 10 mm | 8 mm SD | 8 mm SD | 7 mm PR | 6 mm PR | 7 mm PR |

-continued

| No. | Pathological diagnosis | Lesion | Size of target lesion (baseline) | Size of target lesion (C2) | Size of target lesion (C4) | Size of target lesion (C6) | Size of target lesion (C8) | Size of target lesion (C10) |
|---|---|---|---|---|---|---|---|---|
| C01005 | Liver cancer | Lower lobe of right lung | 16 mm | 16 mm | 9 mm | 7 mm | 5 mm | — |
| | | Upper lobe of right lung | 14 mm | 14 mm | 8 mm | 6 mm | 5 mm | — |
| | | Sum | 30 mm | 30 mm SD | 17 mm PR | 13 mm PR | 10 mm PR | |
| C01013 | Liver cancer | Left liver lobe | 18 mm | 18 mm | 15 mm | — | — | — |
| | | Lower lobe of left lung | 26 mm | 21 mm | 18 mm | — | — | — |
| | | Lower lobe of right lung | 29 mm | 29 mm | 27 mm | — | — | — |
| | | Sum | 73 mm | 68 mm SD | 60 mm SD | — | — | |
| C01015 | Liver cancer | Right liver lobe | 85 mm | 75 mm | 65 mm | — | — | — |
| | | Anterior abdominal wall | 49 mm | 37 mm | 30 mm | — | — | — |
| | | Anterior abdominal wall | 52 mm | 45 mm | 28 mm | — | — | — |
| | | Sum | 186 mm | 157 mm SD | 123 mm PR | — | — | |
| C01019 | Liver cancer | Left liver lobe | 57 mm | 57 mm | 46 mm | — | — | — |
| | | Liver top | 18 mm | 9 mm | 8 mm | — | — | — |
| | | Sum | 75 mm | 66 mm SD | 54 mm SD | — | — | |
| C01020 | Liver cancer | Left liver lobe | 49 mm | 55 mm | 54 mm | — | — | — |
| | | Right liver lobe | 27 mm | 19 mm | 13 mm | — | — | — |
| | | Retroperitoneal lymph node | 37 mm | 36 mm | 33 mm | — | — | — |
| | | Hilar lymph node in liver | 28 mm | 23 mm | 24 mm | — | — | — |
| | | Sum | 141 mm | 133 mm SD | 124 mm SD | — | — | |

Medication: patients C01003, C01005, C01015 and C01020 were administered with a combination of 1200 mg of anti-PD-L1 antibody hu5G11-hIgG1 injection and 10 mg of anlotinib hydrochloride capsule. Patient C01013 was administered with a combination of 1200 mg of anti-PD-L1 antibody hu5G11-hIgG1 injection and 12 mg of anlotinib hydrochloride capsule. Patient C01019 patient was administered with a combination of 1200 mg of anti-PD-L1 antibody hu5G11-hIgG1 injection and 10 mg of anlotinib hydrochloride capsule, and the dose of anlotinib hydrochloride capsule was later reduced to 8 mg.
Patient diagnosis and previous treatment:
Patient C01003: immunohistochemistry: Arg-1(1+), CD34(3+), CK18(2+), GPC3(1+), Hepatocyte(3+), Ki-67(+80%), CD31(3+); intolerant to sorafenib.
Patient C01005: Disease progression after sorafenib treatment.
Patient C01013: Disease progression after surgery and oral lenvatinib capsules.
Patient C01020: intolerant to oral lenvatinib.
Patients C01019 and C01015: no previous standard treatment received.

Example 3. Clinical Trial of Triple Negative Breast Cancer

Example 1. Clinical Trial 3.1 Inclusion Criteria

1) Aged 18-75 years; ECOG physical condition: 0-1; an expected survival of more than 3 months;
2) Histologically or cytologically confirmed recurrent or metastatic triple negative breast cancer, defined as negative for estrogen receptor (ER), progesterone receptor (PR), and human epidermal growth factor receptor (Her-2). ER/PR negative was defined as: ER<1% positive, PR<1% positive. Her-2 negative was defined as: immunohistochemical Her-2(−) or (1+), wherein one with Her-2 (2+) must be subjected to FISH assay and the result should be negative, and one with Her-2(−) or (1+) may be optionally subjected to FISH assay but the result should be negative;
3) Having at least one measurable lesion (RECIST 1.1);
4) At least having received first-line systemic treatment, as well as anthracyclines and/or taxanes, and disease progression after the last treatment; recurrence or disease progression during treatment or within 6 months after the end of treatment should be considered as treatment failure;
5) Laboratory test should meet the follows: blood routine examination: hemoglobin (Hb)≥80 g/L (no blood transfusion within 14 days), absolute neutrophil count (ANC)≥1.5×10$^9$/L and platelet (PLT)≥75×10$^9$/L; biochemical tests: alanine transaminase (ALT) and aspartate transaminase (AST)≤2.5×ULN (for patients with liver metastasis, ≤5×ULN), serum total bilirubin (TBIL)≤1.5×ULN (for patients with Gilbert syndrome, ≤3×ULN), serum creatinine (Cr)≤1.5×ULN and creatinine clearance rate>50 mon; blood coagulation function: activated partial thromboplastin time (APTT), international normalized ratio (INR) and prothrombin time (PT)≤1.5×ULN; doppler ultrasound evaluation: left ventricular ejection fraction (LVEF) ≥50%;
6) Female subjects should agree to take contraceptive measures (such as intrauterine devices [IUD], contraceptives or condoms) during the study and for 6 months after the study; serum or urine pregnancy test results should be negative within 7 days before enrollment, and the subjects must not be breastfeeding; male subjects should agree to take contraceptive measures during the study and for 6 months after the study; and
7) Voluntary participation, written informed consent and good compliance.

3.2 Test Drug

Anti-PD-L1 antibody hu5G11-hIgG1 injection: 1200 mg of anti-PD-L1 antibody injection (100 mg/10 mL) was diluted to 250 mL using normal saline; the diluted drug was administered in 60±5 min by infusion; the infusion system was flushed with normal saline according to the routine requirements of hospitals after the completion of infusion; the injection was administered once every 21 days.

Anlotinib hydrochloride capsule (active ingredient: anlotinib dihydrochloride): 5 minutes before or after the start of anti-PD-L1 antibody infusion, 10 mg of anlotinib hydrochloride capsule was administered orally at fasting; the treatment was given for 2 weeks and interrupted for 1 week, i.e., in 21-day treatment cycles.

Dosage: 12 mg, 10 mg and 8 mg.

3.3 Evaluation Criteria

Disease status was assessed by RECIST 1.1/irRECIST, and mainly by RECIST 1.1 criteria.

3.4 Endpoints

Objective response rate (ORR)=(complete response (CR)+partial response (PR)); Anti-tumor efficacy endpoints: progression-free survival (PFS), disease control rate (DCR=CR+PR+ stable disease (SD)), overall survival (OS), and the like.

3.5 Results

| No. | Size of target lesion (baseline) | Size of target lesion (C2) | Size of target lesion (C4) | Size of target lesion (C6) | Size of target lesion (C8) |
|---|---|---|---|---|---|
| C01001 | 37 mm | 39 mm | 34 mm | 28 mm | 27 mm SD |
| C01003 | 16 mm | 12 mm | 11 mm | 11 mm | 11 mm PR |
| C01004 | 83 mm | 75 mm | 64 mm | 62 mm SD | — |
| C01005 | 55 mm | 56 mm | 55 mm | 60 mm SD | — |
| C01006 | 47 mm | 37 mm | 37 mm SD | — | — |
| C01007 | 15 mm | 15 mm | 15 mm SD | — | — |
| C01008 | 15 mm | 7 mm | 5 mm PR | — | — |
| C01009 | 52 mm | 25 mm | 14 mm PR | — | — |

Medication profile: patients C01001 and C01003 were administered with a combination of 1200 mg of anti-PD-L1 antibody hu5G11-hIgG1 injection and 10 mg of anlotinib hydrochloride capsule. Patients C01004, C01005, C01006, C01007, C01008 and C01009 were administered with a combination of 1200 mg of anti-PD-L1 antibody hu5G11-hIgG1 injection and 12 mg of anlotinib hydrochloride capsule.

Patient conditions:

Patient C01001: Invasive breast cancer in left breast with lymph node metastasis; subjected to radical treatment, chemotherapy (AT regimen (doxorubicin + docetaxel, 3 cycles), AC regimen (doxorubicin + cyclophosphamide, 3 cycles), GP regimen (gemcitabine + carboplatin, 4 cycles)) and radiotherapy (100 Gy, 50 Gy) successively.

Patient C03003: Invasive breast cancer in right breast with lymph node metastasis; subjected to radical treatment, chemotherapy (pirarubicin + cyclophosphamide + docetaxel, 8 cycles)) and radiotherapy successively.

Patient C01004: Invasive breast cancer in right breast with lung metastasis and suspected bone metastasis; subjected to radical treatment, chemotherapy (AC-T regimen (pirarubicin + cyclophosphamide + paclitaxel, 8 cycles), capecitabine (6 cycles), TC regimen (docetaxel + carboplatin, 8 cycles), and docetaxel (2 cycles)) and radiotherapy (50 Gy) successively.

Patient C01005: Invasive breast cancer in right breast with lung and liver metastases; subjected to radical treatment, chemotherapy (AC-T regimen (pirarubicin + cyclophosphamide + paclitaxel, 8 cycles), TX + nimotuzumab (docetaxel + capecitabine, 6 cycles), GP regimen (gemcitabine + cisplatin, 4 cycles), gemcitabine + carboplatin (1 cycle) and IMP4297 capsules (PARP inhibitor)) and radiotherapy successively.

Patient C01006: Invasive breast cancer in right breast; subjected to radical treatment, chemotherapy (TEC regimen (paclitaxel + epirubicin + cyclophosphamide), GP regimen (gemcitabine + cisplatin, 6 cycles), and TX regimen (docetaxel + capecitabine, 1 cycle)) and radiotherapy successively.

Patient C01007: Invasive breast cancer in left breast with lymph node metastasis; subjected to radical treatment, chemotherapy (TC regimen (paclitaxel + carboplatin, 6 cycles), and paclitaxel + capecitabine (3 cycles)) and radiotherapy (223.4 Gy) successively.

Patient C01008: Invasive breast cancer in left breast; subjected to radical treatment, chemotherapy (EC-T regimen (epirubicin + cyclophosphamide + paclitaxel, 8 cycles)) and radiotherapy successively.

Patient C01009: Invasive ductal carcinoma in left breast with lymph node metastasis; subjected to radical treatment and chemotherapy (TAC regimen (pirarubicin + cyclophosphamide + paclitaxel, 6 cycles), paclitaxel (9 cycles), and carboplatin (1 cycle)) successively.

Example 4. Clinical Trial of Lung Cancer

4.1 Inclusion Criteria

1) Aged≥18 years; ECOG physical condition: 0-1; an expected survival of more than 3 months;
2) Histologically or cytologically confirmed non-small cell lung cancer;
3) Patients with advanced disease (stage IIIB/IV) who had received at least first-line standard chemotherapy but failed or were intolerant to chemotherapy, and at least one measurable lesion according to the Response Evaluation Criteria in Solid Tumors RECIST 1.1;
4) Tumor expressing PD-L1 positive (tumor proportion score TPS≥1%).

Tissue sample: formalin-fixed, paraffin-embedded tumor samples for PD-L1 analysis. Tissue samples must be received and evaluated by a central service provider before randomization Fine needle aspirates were not accepted. Core needle biopsy or excision samples, or excised tissues were accepted;

5) Normal main organ functions meeting the following criteria:
   a) Blood Routine Examination: hemoglobin (Hb)≥90 g/L (no blood transfusion within the last 14 days); absolute neutrophil count (ANC)≥1.5×10$^9$/L; platelet count (PLT)≥80×10$^9$/L;
   b) Biochemical Tests: alanine transaminase (ALT) and aspartate transaminase (AST)≤2.5×ULN (for patients with tumor liver metastasis, ≤5×ULN); total bilirubin (TBIL) in serum≤1.5×ULN (for patients with Gilbert syndrome, ≤3×ULN); serum creatinine (Cr)≤1.5×ULN, or calculated creatinine clearance rate≥50 mL/min;

Creatinine clearance rate: Ccr=(140−age)×weight (kg)/72×Scr (mg/dL)

Ccr=[(140−age)×body weight (kg)/[0.818×Scr (μmol/L)]

For female subjects, the calculated rate should be multiplied by 0.85; 1 mg/dL=88.41 μmon.

c) Blood coagulation: activated partial thromboplastin time (APTT), international normalized ratio (INR), prothrombin time (PT)≤1.5×ULN;

6) Female subjects should agree to take contraceptive measures (such as intrauterine devices [IUD], contraceptives or condoms) during the study and for 6 months after the study; serum or urine pregnancy test results should be negative within 7 days before enrollment, and the subjects must not be breastfeeding; male subjects should agree to take contraceptive measures during the study and for 6 months after the study; and
7) Voluntary participation, written informed consent and good compliance.

4.2 Exclusion Criteria

1) Previous use of anlotinib hydrochloride, other anti-PD-1/PD-L1 antibody, or other immunotherapies against PD-1/PD-L1;
2) Severe hypersensitivity after receiving other monoclonal antibodies;
3) Other malignant tumors currently or within 5 years (except for cured basal cell carcinoma and cervical carcinoma in situ);
4) Any active autoimmune disease or a history of autoimmune disease (for example, but not limited to: autoimmune hepatitis, interstitial pneumonia, enteritis, vasculitis, nephritis; subjects with asthma requiring medical intervention with bronchodilators cannot be included); but the following subjects were allowed to be enrolled: vitiligo, psoriasis and alopecia requiring no systemic treatment, well controlled type I diabetes, and hypothyroidism with normal thyroid function after hormone replacement therapy;
5) Current use of immunosuppressants, or systemic therapy for immunosuppression (>10 mg/day of prednisone or other hormones with equal efficacy) within 2 weeks prior to the first dose;
6) Factors affecting oral administration (such as inability to swallow, gastrointestinal resection, chronic diarrhea and intestinal obstruction);
7) Uncontrolled pleural effusion, pericardial effusion or ascites requiring continuous drainage; 8) Radiologically (CT or MRI) confirmed tumor invasion in large blood vessels or unclear demarcation from large blood vessels;
9) Any bleeding or hemorrhage events CTCAE grade≥3 within 4 weeks prior to the first dose, or presence of nonhealing wounds, ulcers or fractures;
10) Uncontrolled brain metastasis symptoms, spinal cord compression, carcinomatous meningitis, or CT or MRI confirmed disease in brain or pia mater within 8 weeks prior to the first dose;
11) Previous radiotherapy, chemotherapy and surgery less than 4 weeks, or oral targeted therapy less than 5 half-lives from the first study dose; oral fluorouracil less than 14 days, or mitomycin C and nitrosourea less than 6 weeks; or patients with adverse events (other than alopecia) that did not return to CTCAE grade≤1 caused by previous treatment;
12) Any severe and/or uncontrolled disease, including:
a) Unsatisfactory blood pressure control (systolic pressure≥150 mmHg, diastolic pressure≥90 mmHg);
b) Unstable angina pectoris, myocardial infarction, congestive heart failure grade≥2, or arrhythmia requiring intervention (including QTc≥480 ms) within 6 months before the first dose;
c) Active or uncontrolled severe infections (CTCAE grade≥2 infection);
d) Cirrhosis, decompensated hepatic disease, active hepatitis or chronic hepatitis requiring antiviral treatment;
*Active hepatitis (hepatitis B: HBsAg positive and an HBV DNA measure greater than upper limit of normal; hepatitis C: HCV antibody positive and an HCV virus titer greater than upper limit of normal);
e) HIV positive;
f) Inadequate control of diabetes mellitus (fasting blood glucose CTCAE grade≥2);
g) Routine urinalysis suggesting urine protein≥++, and protein urine 24 hour>1.0 g.
13) Vaccination or attenuated vaccination within 4 weeks before the first dosing.
14) Other factors that may lead to withdrawal according to the judgment of investigator, for example, other serious diseases (including mental diseases) requiring concomitant therapy, serious laboratory abnormality, family or social factors that may affecting the safety of the subject or data acquisition and sample collection.

4.3 Test Drug

Anti-PD-L1 antibody hu5G11-hIgG1 injection: 1200 mg of anti-PD-L1 antibody injection (100 mg/10 mL) was diluted to 250 mL using normal saline; the diluted drug was administered in 60±5 min by infusion; the infusion system was flushed with normal saline according to the routine requirements of hospitals after the completion of infusion; the injection was administered once every 21 days.

Anlotinib hydrochloride capsule (active ingredient: anlotinib dihydrochloride): 5 minutes before or after the start of anti-PD-L1 antibody infusion, 10 mg of anlotinib hydrochloride capsule was administered orally at fasting; the treatment was given for 2 weeks and interrupted for 1 week, i.e., in 21-day treatment cycles.

Specification: 12 mg, 10 mg and 8 mg.

4.4 Evaluation Criteria

Disease status was assessed by RECIST 1.1/irRECIST, and mainly by RECIST 1.1 criteria.

4.5 Endpoints

Progression-Free Survival (PFS);

Anti-tumor efficacy endpoints: Objective response rate (ORR)=(complete response (CR)+partial response (PR)), disease control rate (DCR=CR+PR+ stable disease (SD)), overall survival (OS), and the like.

4.6 Results

| No. | Size of target lesion (baseline) | Size of target lesion (C2) | Size of target lesion (C4) | Size of target lesion (C6) | Size of target lesion (C8) |
|---|---|---|---|---|---|
| 01 | 70 mm | 56 mm | 55 mm | 45 mm | 45 mm PR |
| 08 | 82 mm | 78 mm | 75 mm | 75 mm SD | — |
| 011 | 41 mm | 28 mm | 28 mm PR | — | — |

Patient Conditions:

Patient 01: Medium to poorly differentiated adenocarcinoma in left upper lung with metastases in lymph nodes and lateral lungs. Genotype: BRAF p.V600E.

Patient 08: Adenocarcinoma in left lung. Genotype: EGFR del/EGFR-T790M.

Patient 011: Recurrent adenocarcinoma in lung (stage IVA) with metastasis. Genotype: EGFR.

In the above examples, each treatment cycle took 21 days, and C2, C4, C6, C8 and C10 indicate 2 cycles, 4 cycles, 6 cycles, 8 cycles and 10 cycles, respectively. In the above examples, the target lesion size (baseline) refers to the longest radiographic diameter of the target lesion before the study treatment.

What is claimed is:

1. A combination comprising an anti-PD-L1 antibody and anlotinib, wherein the anti-PD-L1 antibody comprises an amino acid sequence as follows: a heavy chain CDR1 region having an amino acid sequence set forth in SEQ ID NO: 1; a heavy chain CDR2 region having an amino acid sequence set forth in SEQ ID NO: 2; a heavy chain CDR3 region having an amino acid sequence set forth in SEQ ID NO: 3; a light chain CDR1 region having an amino acid sequence set forth in SEQ ID NO: 7; a light chain CDR2 region having an amino acid sequence set forth in SEQ ID NO: 8; and a light chain CDR3 region having an amino acid sequence set forth in SEQ ID NO: 9.

2. The combination according to claim 1, wherein the combination is used for treating a tumor in biliary system, liver cancer, triple negative breast cancer or lung cancer.

3. The combination according to claim 1, wherein the combination comprises a pharmaceutical composition of the anti-PD-L1 antibody and a pharmaceutical composition of anlotinib.

4. The combination according to claim 1, wherein the combination is packaged in a kit further comprising an instruction for combined use of the anti-PD-L1 antibody and anlotinib in treating a tumor in biliary system, liver cancer, triple negative breast cancer and/or lung cancer.

5. The combination according to claim 1, wherein the combination comprises a pharmaceutical composition containing 600-2400 mg of the anti-PD-L1 antibody and a pharmaceutical composition containing anlotinib in a single dose of 6 mg, 8 mg, 10 mg and/or 12 mg.

6. The combination according to claim 1, wherein the combination comprises the anti-PD-L1 antibody and the anlotinib in a weight ratio of (0.35-29):1.

7. The combination according to claim 1, wherein the combination is a formulation suitable for administration within a single treatment cycle, comprising a pharmaceutical composition containing 600-2400 mg of the anti-PD-L1 antibody and a pharmaceutical composition containing 84-168 mg of anlotinib.

8. A method for treating a tumor in biliary system, liver cancer, triple negative breast cancer and/or lung cancer, comprising administering to a subject an effective amount of an anti-PD-L1 antibody and anlotinib, wherein the anti-PD-L1 antibody comprises an amino acid sequence as follows: a heavy chain CDR1 region having an amino acid sequence set forth in SEQ ID NO: 1; a heavy chain CDR2 region having an amino acid sequence set forth in SEQ ID NO: 2; a heavy chain CDR3 region having an amino acid sequence set forth in SEQ ID NO: 3; a light chain CDR1 region having an amino acid sequence set forth in SEQ ID NO: 7; a light chain CDR2 region having an amino acid sequence set forth in SEQ ID NO: 8; and a light chain CDR3 region having an amino acid sequence set forth in SEQ ID NO: 9.

9. The method according to claim 8, wherein the anti-PD-L1 antibody and anlotinib are packaged separately.

10. The method according to claim 9, wherein the anti-PD-L1 antibody and anlotinib are each in the form of a pharmaceutical composition that can be administered simultaneously, sequentially or at intervals.

11. The method according to claim 9, wherein the anti-PD-L1 antibody is administered once every week, every 2 weeks, every 3 weeks, or every 4 weeks at a dose of 600-2400 mg.

12. The method according to claim 9, wherein anlotinib is administered at a dose of 6 mg, 8 mg, 10 mg, or 12 mg once daily with a regimen of 2-week treatment and 1-week interruption.

13. A kit for use in treating a tumor in biliary system, liver cancer, triple negative breast cancer and/or lung cancer, comprising a pharmaceutical composition of an anti-PD-L1 antibody, a pharmaceutical composition of anlotinib, and an instruction for combined use of the anti-PD-L1 antibody and anlotinib in treating a tumor in biliary system, liver cancer, triple negative breast cancer and/or lung cancer, wherein the anti-PD-L1 antibody comprises an amino acid sequence as follows: a heavy chain CDR1 region having an amino acid sequence set forth in SEQ ID NO: 1; a heavy chain CDR2 region having an amino acid sequence set forth in SEQ ID NO: 2; a heavy chain CDR3 region having an amino acid sequence set forth in SEQ ID NO: 3; a light chain CDR1 region having an amino acid sequence set forth in SEQ ID NO: 7; a light chain CDR2 region having an amino acid sequence set forth in SEQ ID NO: 8; and a light chain CDR3 region having an amino acid sequence set forth in SEQ ID NO: 9.

14. The kit according to claim 13, wherein the kit is suitable for administration within a single treatment cycle, comprising a pharmaceutical composition containing 600-2400 mg of the anti-PD-L1 antibody and a pharmaceutical composition containing 84-168 mg of anlotinib.

15. The combination according to claim 1, wherein the anti-PD-L1 antibody comprises an amino acid sequence as follows: a heavy chain variable region having an amino acid sequence set forth in SEQ ID NO: 13; and a light chain variable region having an amino acid sequence set forth in SEQ ID NO: 15.

16. The combination according to claim 1, wherein the anti-PD-L1 antibody comprises: a heavy chain amino acid sequence set forth in SEQ ID NO: 17; and a light chain amino acid sequence set forth in SEQ ID NO: 18; or a heavy chain amino acid sequence set forth in SEQ ID NO: 21; and a light chain amino acid sequence set forth in SEQ ID NO: 18.

17. The combination according to claim 1, wherein anlotinib is in the form of a free base, or in the form of a pharmaceutically acceptable salt thereof.

18. The combination according to claim 1, wherein the anti-PD-L1 antibody and anlotinib in the combination are packaged separately.

19. The method according to claim 8, wherein the anti-PD-L1 antibody comprises an amino acid sequence as follows: a heavy chain variable region having an amino acid sequence set forth in SEQ ID NO: 13; and a light chain variable region having an amino acid sequence set forth in SEQ ID NO: 15.

20. The method according to claim 8, wherein the anti-PD-L1 antibody comprises: a heavy chain amino acid sequence set forth in SEQ ID NO: 17; and a light chain amino acid sequence set forth in SEQ ID NO: 18; or a heavy chain amino acid sequence set forth in SEQ ID NO: 21; and a light chain amino acid sequence set forth in SEQ ID NO: 18.

* * * * *

UNITED STATES PATENT AND TRADEMARK OFFICE
CERTIFICATE OF CORRECTION

PATENT NO. : 12,421,313 B2
APPLICATION NO. : 17/425006
DATED : September 23, 2025
INVENTOR(S) : Xiquan Zhang et al.

It is certified that error appears in the above-identified patent and that said Letters Patent is hereby corrected as shown below:

On the Title Page

At (73) Assignee, please delete "Chia Tia Tianqing Pharmaceutical Group Co., Ltd." and please insert --Chia Tai Tianqing Pharmaceutical Group Co., Ltd.-- therefor.

Signed and Sealed this
Thirtieth Day of December, 2025

John A. Squires
*Director of the United States Patent and Trademark Office*

SEQUENCE LISTING

<160> NUMBER OF SEQ ID NOS: 21

<210> SEQ ID NO 1
<211> LENGTH: 5
<212> TYPE: PRT
<213> ORGANISM: Mus sp.

<400> SEQUENCE: 1

```
Thr Tyr Gly Val His
1               5

<210> SEQ ID NO 2
<211> LENGTH: 16
<212> TYPE: PRT
<213> ORGANISM: Mus sp.

<400> SEQUENCE: 2

Val Ile Trp Arg Gly Val Thr Thr Asp Tyr Asn Ala Ala Phe Met Ser
1               5                  10                  15

<210> SEQ ID NO 3
<211> LENGTH: 8
<212> TYPE: PRT
<213> ORGANISM: Mus sp.

<400> SEQUENCE: 3

Leu Gly Phe Tyr Ala Met Asp Tyr
1               5

<210> SEQ ID NO 4
<211> LENGTH: 5
<212> TYPE: PRT
<213> ORGANISM: Mus sp.

<400> SEQUENCE: 4

Ser Tyr Gly Met Ser
1               5

<210> SEQ ID NO 5
<211> LENGTH: 16
<212> TYPE: PRT
<213> ORGANISM: Mus sp.

<400> SEQUENCE: 5

Ser Ile Ser Ser Gly Gly Ser Thr Tyr Tyr Pro Asp Ser Val Lys Gly
1               5                  10                  15

<210> SEQ ID NO 6
<211> LENGTH: 8
<212> TYPE: PRT
<213> ORGANISM: Mus sp.

<400> SEQUENCE: 6

Gly Tyr Asp Ser Gly Phe Ala Tyr
1               5

<210> SEQ ID NO 7
<211> LENGTH: 11
<212> TYPE: PRT
<213> ORGANISM: Mus sp.

<400> SEQUENCE: 7

Lys Ala Ser Gln Ser Val Ser Asn Asp Val Ala
1               5                  10

<210> SEQ ID NO 8
<211> LENGTH: 7
<212> TYPE: PRT
<213> ORGANISM: Mus sp.

<400> SEQUENCE: 8

Tyr Ala Ala Asn Arg Tyr Thr
```

```
<210> SEQ ID NO 9
<211> LENGTH: 9
<212> TYPE: PRT
<213> ORGANISM: Mus sp.

<400> SEQUENCE: 9

Gln Gln Asp Tyr Thr Ser Pro Tyr Thr
1               5

<210> SEQ ID NO 10
<211> LENGTH: 14
<212> TYPE: PRT
<213> ORGANISM: Mus sp.

<400> SEQUENCE: 10

Ala Ser Gln Ser Val Ser Thr Ser Ser Ser Phe Met His
1               5                   10

<210> SEQ ID NO 11
<211> LENGTH: 7
<212> TYPE: PRT
<213> ORGANISM: Mus sp.

<400> SEQUENCE: 11

Tyr Ala Ser Asn Leu Glu Ser
1               5

<210> SEQ ID NO 12
<211> LENGTH: 9
<212> TYPE: PRT
<213> ORGANISM: Mus sp.

<400> SEQUENCE: 12

Gln His Ser Trp Glu Ile Pro Tyr Thr
1               5

<210> SEQ ID NO 13
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Ile Thr Leu Lys Glu Ser Gly Pro Thr Leu Val Lys Pro Thr Gln
1               5                   10                  15

Thr Leu Thr Leu Thr Cys Thr Val Ser Gly Phe Ser Leu Ser Thr Tyr
            20                  25                  30

Gly Val His Trp Ile Arg Gln Pro Pro Gly Lys Ala Leu Glu Trp Leu
        35                  40                  45

Gly Val Ile Trp Arg Gly Val Thr Thr Asp Tyr Asn Ala Ala Phe Met
    50                  55                  60

Ser Arg Leu Thr Ile Thr Lys Asp Asn Ser Lys Asn Gln Val Val Leu
65                  70                  75                  80

Thr Met Asn Asn Met Asp Pro Val Asp Thr Ala Thr Tyr Tyr Cys Ala
                85                  90                  95

Arg Leu Gly Phe Tyr Ala Met Asp Tyr Trp Gly Gln Gly Thr Leu Val
            100                 105                 110

Thr Val Ser Ser
```

-continued

```
            115

<210> SEQ ID NO 14
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Arg Ser Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Asp Cys Ala
                85                  90                  95

Arg Gly Tyr Asp Ser Gly Phe Ala Tyr Trp Gly Gln Gly Thr Leu Val
            100                 105                 110

Thr Val Ser Ser
        115

<210> SEQ ID NO 15
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Ala Ala Asn Arg Tyr Thr Gly Val Pro Asp Arg Phe Ser Gly
    50                  55                  60

Ser Gly Tyr Gly Thr Asp Phe Thr Phe Thr Ile Ser Ser Leu Gln Pro
65                  70                  75                  80

Glu Asp Ile Ala Thr Tyr Phe Cys Gln Gln Asp Tyr Thr Ser Pro Tyr
                85                  90                  95

Thr Phe Gly Gln Gly Thr Lys Leu Glu Ile Lys
            100                 105

<210> SEQ ID NO 16
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16
```

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Gln Ser Val Ser Thr Ser
            20                  25                  30

Ser Ser Ser Phe Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Ser Trp
                85                  90                  95

Glu Ile Pro Tyr Thr Phe Gly Gln Gly Thr Lys Leu Glu Ile Lys
            100                 105                 110
```

<210> SEQ ID NO 17
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Gln Ile Thr Leu Lys Glu Ser Gly Pro Thr Leu Val Lys Pro Thr Gln
1               5                   10                  15

Thr Leu Thr Leu Thr Cys Thr Val Ser Gly Phe Ser Leu Ser Thr Tyr
            20                  25                  30

Gly Val His Trp Ile Arg Gln Pro Pro Gly Lys Ala Leu Glu Trp Leu
        35                  40                  45

Gly Val Ile Trp Arg Gly Val Thr Thr Asp Tyr Asn Ala Ala Phe Met
    50                  55                  60

Ser Arg Leu Thr Ile Thr Lys Asp Asn Ser Lys Asn Gln Val Val Leu
65                  70                  75                  80

Thr Met Asn Asn Met Asp Pro Val Asp Thr Ala Thr Tyr Tyr Cys Ala
                85                  90                  95

Arg Leu Gly Phe Tyr Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
```

```
                   245                 250                 255
Glu Val Thr Cys Val Val Val Ala Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 18
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Ala Ala Asn Arg Tyr Thr Gly Val Pro Asp Arg Phe Ser Gly
    50                  55                  60

Ser Gly Tyr Gly Thr Asp Phe Thr Phe Thr Ile Ser Ser Leu Gln Pro
65                  70                  75                  80

Glu Asp Ile Ala Thr Tyr Phe Cys Gln Gln Asp Tyr Thr Ser Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 19
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Arg Ser Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Asp Cys Ala
            85                  90                  95

Arg Gly Tyr Asp Ser Gly Phe Ala Tyr Trp Gly Gln Gly Thr Leu Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Ala Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
                435                 440                 445

<210> SEQ ID NO 20
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Val Leu Thr Gln Ser Pro Ala Ser Leu Ala Val Ser Pro Gly
1               5                   10                  15

Gln Arg Ala Thr Ile Thr Cys Arg Ala Ser Gln Ser Val Ser Thr Ser
            20                  25                  30

Ser Ser Ser Phe Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Ser Trp
                85                  90                  95

Glu Ile Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
```

-continued

```
                210                 215

<210> SEQ ID NO 21
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Ile Thr Leu Lys Glu Ser Gly Pro Thr Leu Val Lys Pro Thr Gln
1               5                   10                  15

Thr Leu Thr Leu Thr Cys Thr Val Ser Gly Phe Ser Leu Ser Thr Tyr
            20                  25                  30

Gly Val His Trp Ile Arg Gln Pro Pro Gly Lys Ala Leu Glu Trp Leu
        35                  40                  45

Gly Val Ile Trp Arg Gly Val Thr Thr Asp Tyr Asn Ala Ala Phe Met
    50                  55                  60

Ser Arg Leu Thr Ile Thr Lys Asp Asn Ser Lys Asn Gln Val Val Leu
65                  70                  75                  80

Thr Met Asn Asn Met Asp Pro Val Asp Thr Ala Thr Tyr Tyr Cys Ala
                85                  90                  95

Arg Leu Gly Phe Tyr Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350
```

-continued

```
Glu Met Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
    370             375                 380
Asn Asn Tyr Lys Thr Thr Pro Pro Val Leu Asp Ser Asp Gly Ser Phe
385             390                 395                 400
Phe Leu Tyr Ser Arg Leu Thr Val Asp Lys Ser Arg Trp Gln Glu Gly
                405                 410                 415
Asn Val Phe Ser Cys Ser Val Met His Glu Ala Leu His Asn His Tyr
            420                 425                 430
Thr Gln Lys Ser Leu Ser Leu Ser Leu Gly
        435                 440
```